United States Patent [19]
Wren

[11] Patent Number: 6,037,344
[45] Date of Patent: *Mar. 14, 2000

[54] COMPOSITIONS AND METHODS FOR CONTROLLING PEST INSECTS

[75] Inventor: Heather N. Wren, Hampstead, N.C.

[73] Assignee: Virginia Tech Intellectual Properties, Inc., Blacksburg, Va.

[ * ] Notice: This patent is subject to a terminal disclaimer.

[21] Appl. No.: 08/795,983

[22] Filed: Feb. 5, 1997

Related U.S. Application Data

[63] Continuation-in-part of application No. 08/595,899, Feb. 6, 1996, Pat. No. 5,770,601, which is a continuation-in-part of application No. 08/291,072, Aug. 17, 1994, Pat. No. 5,514,681.

[51] Int. Cl.[7] .......................... A01N 43/42; A01N 43/54; A01N 43/90
[52] U.S. Cl. ........................ 514/258; 424/84; 514/262; 514/263; 514/264; 514/275; 514/278
[58] Field of Search ................................. 514/258, 262, 514/263, 264, 275, 278; 424/84

[56] References Cited

U.S. PATENT DOCUMENTS

| | | | |
|---|---|---|---|
| 4,857,532 | 8/1989 | Koehler et al. | 514/262 |
| 4,883,801 | 11/1989 | Nathanson | 514/263 |
| 4,902,690 | 2/1990 | Nathanson | 514/213 |

*Primary Examiner*—Allen J. Robinson
*Attorney, Agent, or Firm*—Pennie & Edmonds LLP

[57] ABSTRACT

Compositions of a purine, a xanthine oxidase inhibitor and/or a dihydrofolate reductase inhibitor, and methods of using same, for controlling the growth of pest insects which salvage, store, or excrete their nitrogenous wastes via the purine metabolic pathway.

21 Claims, 1 Drawing Sheet

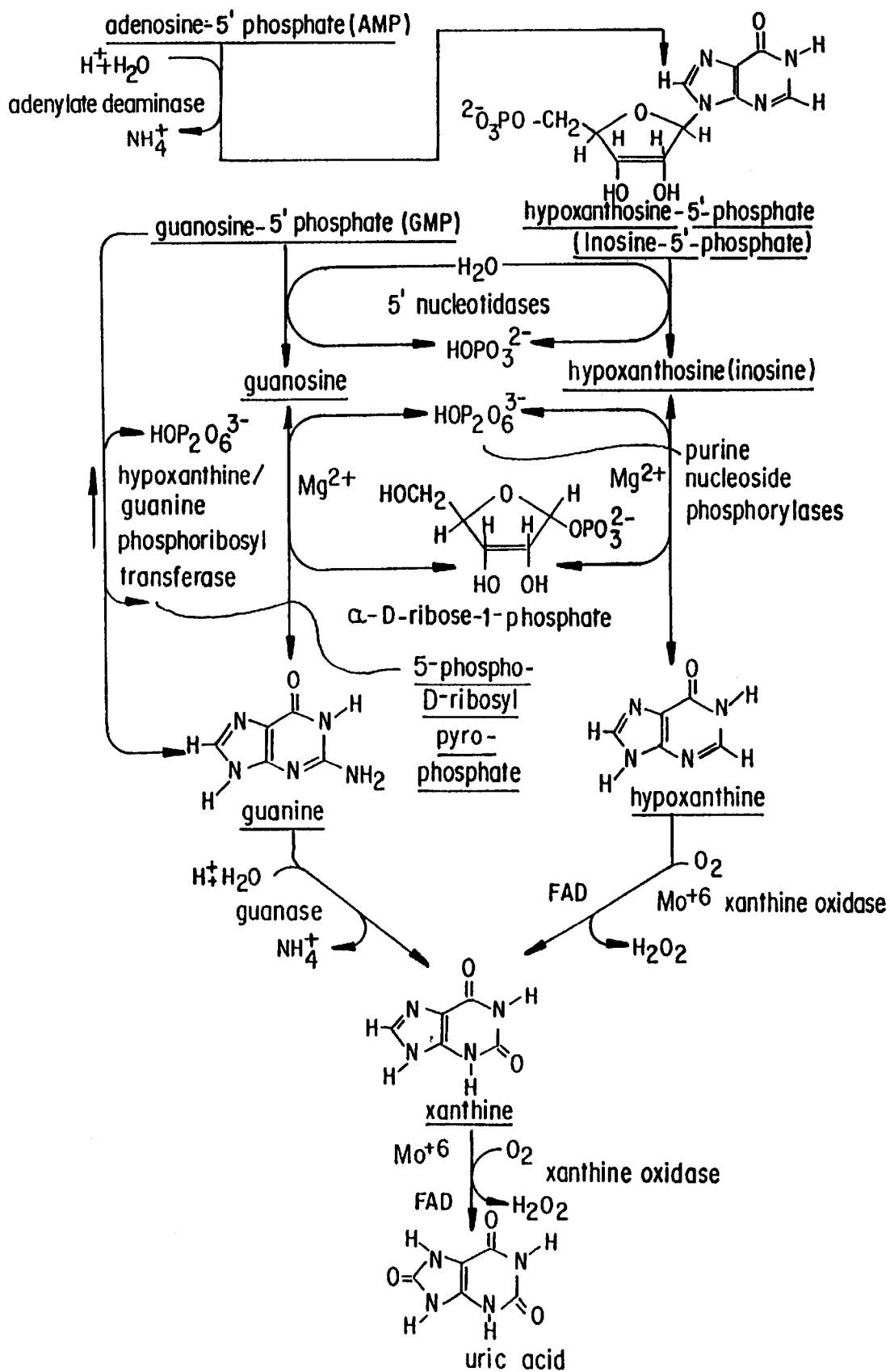

COMPOSITIONS AND METHODS FOR CONTROLLING PEST INSECTS

This application is a continuation-in-part of U.S. patent application Ser. No. 08/595,899, filed Feb. 6, 1996, now U.S. Pat. No. 5,770,601, issued Jun. 23, 1998, which is a continuation-in-part of U.S. patent application Ser. No. 08/291,072, filed Aug. 17, 1994, now U.S. Pat. No. 5,514,681, issued May 7, 1996, each of which is hereby incorporated by reference in its entirety.

BACKGROUND OF INVENTION

1. Field of the Invention

The present invention is directed to the regulation of the growth of pest insects which utilize the purine metabolic pathway to salvage, store, or excrete their nitrogenous wastes. It comprises bringing into contact with the pest insects, formulations containing growth-controlling amounts of compositions comprising purines, purine metabolic-enzyme inhibitors, and inhibitors of enzymes which regulate production of specific co-factors of this pathway.

2. Description of the Background Art

Despite the recent development and great promise of such advanced insect-controlling techniques as chemical sterilants, pheromones, and ecologically-based control strategies, the use of chemical insecticides still plays a predominant role. However, rising public awareness of environmental issues, more stringent government regulations, and increasing insect resistance to conventional modalities are driving the pest control industry to seek safer alternatives to these conventional chemical insecticides.

Others have attempted to identify and evaluate the efficacy of insect growth inhibitors. However, given the continuous need for increased selectivity and effectiveness of insect control agents, it became desirable to engage in rational formulation of control agents based on an understanding of key insect nutritional and metabolic pathways.

SUMMARY OF THE INVENTION

It is widely acknowledged that the majority of insects are uricotelic in that they excrete their excess nitrogen as uric acid and uricolytic derivatives thereof (Cochran (1975), "Excretion in Insects" in *Insect Biochemistry and Function* pp. 171–281). The uric acid is synthesized, via the purine catabolic pathway shown in FIG. 1, and is either excreted to the outside, or, in some cases, stored by the insect as a metabolic reserve.

Cockroaches are a good model of the essential nature of storage-excretion of uric acid. For example, in German cockroaches, a slurry of uric acid is passed to the female during mating, as a paternal investment. The female, in turn, invests the developing eggs with a supply of uric acid that is used during embryogenesis (Mullins & Keil (1980), *Nature* 283: 567–569). Interruption of this vital cycle appears highly detrimental to cockroach population growth, which depends heavily on these uric acid stores (Engebretson & Mullins (1986), *Comp. Biochem. Physiol.* 83B: 93–97; Suiter et al. (1992), *J. Econ. Entomol.* 85(1): 117–122). In the cockroach fat body, de novo synthesis of uric acid takes place, largely through purine salvage, in the trophocytes and the uric acid is stored in specialized urocytes for recycling (Cochran (1985), *Ann. Rev. Entomol.* 30: 29–49). This is accomplished through uricolytic digestion of the stored urates by endosymbiont bacteria which are sequestered in bacteriocyte cells adjacent to the urocytes (Wren & Cochran (1987), *Comp. Biochem. Physiol.* 88B: 1023–1026). In this part of the uric acid cycle, the endosymbiont bacteria use xanthine dehydrogenase to reduce the urates to xanthine, and disruption of any part of this system also inhibits population growth.

Another essential facet of insect physiology is the molt cycle, when the cuticular epithelial cells multiply and synthesize a new, larger exoskeleton just prior to ecdysis (Chapman (1982), *The Insects Structure and Function.* Cambridge, Mass.: Harvard University Press; Hepburn (1985), "The Integument" in *Fundamentals of Insect Physiology.* Ed. M. S. Blum, pp. 139–183. New York: John Wiley & Sons, Inc.). At the same time, many of the internal tissues are growing, as in cockroaches where, for example, development of the internal and external reproductive organs progresses with each stage, culminating at the final molt to the sexually mature adult (Chapman (1982) *The Insects Structure and Function*, Cambridge Mass.: Harvard University Press). During this process, insects draw heavily on their metabolic reserves to achieve the rapid growth of cells which takes place.

The purine metabolic pathway is central to all of these processes, and, thus, to homeostasis of insects. As in any of the known biochemical pathways, the hydrolytic enzymes and their co-factors are essential to the functioning of the purine degradative pathway. This pathway also serves to salvage the free purine bases for re-use in nucleotide and nucleic acid biosynthesis (Lehninger (1970) Biochemistry: The Molecular Basis of Cell Structure and Function 2nd Ed. pp. 740–742).

Two of the enzymes involved in this pathway are xanthine oxidase and dihydrofolate reductase (also known as tetrahydrofolate dehydrogenase). Xanthine oxidase (E.C. 1.2.3.2), a molybdenum iron sulfur flavo-enzyme, functions late in the salvage pathway of purine catabolism from guanosine monophosphate and inosine monophosphate to xanthine, and finally, to uric acid. In this pathway, xanthine oxidase catalyzes both the conversion of hypoxanthine to xanthine, and the conversion of xanthine to uric acid (Coughlan (1980) *Molybdenum and Molybdenum-Containing Enzymes.* New York: Pergamon Press). Functioning as xanthine dehydrogenase, the same enzyme reduces uric acid to xanthine in the uricolytic pathway of the endosymbiont bacteria in the cockroach fat body (Wren & Cochran (1987), *Comp. Biochem. Physiol.* 88B: 1023–1026). Dihydrofolate reductase catalyzes the synthesis of tetrahydrofolate, which is an essential co-factor in the uric acid and purine synthesis pathways (Kucers & Bennett (1979), "Trimethoprim and Cotrimoxazole" in *The Use of Antibiotics.* 3rd Ed. London: William Heinemann Medical Books, Ltd.).

An understanding of these insect systems, which rely on the recycling and excretion of their purines, led to the present invention, which provides novel compositions and methods for disrupting insect homeostasis and inhibiting insect population growth. Thus, in one embodiment, these compositions comprise (1) a purine such as guanine (2-amino-1,7-dihydro-6H-purin-6-one); hypoxanthine (1,7-dihydro-6H-purin-6-one); xanthine (3,7-dihydro-1H-purine-2,6-dione), or uric acid, and mixtures thereof, and (2) a xanthine oxidase inhibitor, preferably one of the pyrazolo [3,4-d]pyrimidine group, such as oxypurinol (4,6-dihydroxypyrazolo[3,4-d]pyrimidine); allopurinol (4-hydroxypyrazolo[3,4-d]pyrimidine); mercapto-allopurinol (4-hydroxy-6-mercaptopyrazolo[3,4-d] pyrimidine); 4-mercapto-6-hydroxypyrazolo[3,4-d] pyrimidine; 4,6-dimercaptopyrazolo[3,4-d]pyrimidine; or 4-amino-6-hydroxypyrazolo[3,4-d]pyrimidine; and mixtures thereof. In another embodiment, these compositions comprise (1) a purine; (2) a xanthine oxidase inhibitor; and (3) a dihydrofolate reductase inhibitor such as trimethoprim (2,4-diamino-5-(3,4,5-trimethoxybenzyl)-pyrimidine), methotrexate (N-[4-[[(2,4-diamino-6-pteridinyl)methyl]

methylamino]benzoyl]-L-glutamic acid), or pyrimethamine (5-(4-chlorophenyl)-6-ethyl-2,4-pyrimidinediamine), and mixtures thereof.

While specific purines in combination with specific enzyme inhibitors are utilized to illustrate the present invention, it is understood that any of the purines and inhibitors of any of the enzymes of the pathway of FIG. 1 may be applied according to the present invention.

Furthermore, while cockroaches, termites, mole crickets, house flies, and carpenter ants are utilized to illustrate the present invention, it is understood that the compositions and methods of the present invention may be applied to regulate the growth of any pest insect which utilizes the purine metabolic pathway to salvage, store, or excrete to the outside, its nitrogen wastes.

A further embodiment of the invention comprises an insect bait or attractant formulation containing an insect-growth-regulating effective amount of the compositions.

DESCRIPTION OF THE FIGURES

FIG. 1 shows the pathway for purine catabolism.

DETAILED DESCRIPTION OF THE INVENTION

The present invention is predicated on the discovery that ingestion of formulations containing growth controlling amounts of certain novel compositions by pest insects, particularly cockroaches, termites, mole crickets, house flies, and carpenter ants, disrupts homeostasis and inhibits population growth.

The compositions of the present invention may be the sole active ingredients of the formulation or they may be admixed with one or more additional active ingredients, such as other, conventional insecticides.

The compositions of the present invention may be formulated with a "bait" or "attractant." For purposes of description of the present invention, these terms refer to any formulation to which pest insects are attracted and which they will ingest. Such compositions are well-known to those skilled in the art and it will be understood that any such material which is inert with respect to the compositions of the present invention may be employed in the practice of the invention.

In use, the formulations may be applied to the pest insects, to the locus of the pest insects, and/or to the habitat of the pest insects.

The following examples are included for purposes of illustration only and are not intended to be limiting, unless otherwise specified.

EXAMPLE 1

General Procedure

Unless otherwise specified, German cockroaches (*Blattella germanica* L.) from the stock laboratory "VPI" strain were used to form experimental colonies of mixed life stages. Unless otherwise specified, each insect colony of 42 insects contained five each of newly post-emergent adult males and females, eight each of male and female nymphs at the fifth nymphal stage, and eight each of male and female nymphs at the third nymphal stage. Care was taken to select insects from the same stock colonies for each experimental block, and each colony was allowed to acclimatize for twenty-four (24) hours prior to treatment.

The colonies were housed in one-gallon glass battery jars fitted with fiber-board platforms, with clean tap-water offered continuously in cotton-stoppered glass vials. The jars were rimmed with a thin coating of petrolatum, and covered closely with three layers of cheesecloth held in place with strong elastic bands. These measures prevented escape of the test insects, as well as contamination by other insects.

Each test included "control" colonies, in which the food was untreated, and "test" colonies, in which the food was mixed with the compositions being tested to form percent concentrations by weight (w/w). Unless otherwise specified, the food was Agway Laboratory Rat Chow and was prepared by grinding the chow pellets to a fine powder and, for test colonies, incorporating the test compositions by grinding and mixing them with the chow, using a mortar and pestle. In some cases, as specified more fully in the examples, the test compositions were incorporated into food which consisted of an inert bait base, which would be known to one of ordinary skill in the art, or a 50% (w/w) inert bait-base+rat chow composition. Food, either treated or untreated, was pre-weighed in stainless steel planchettes and offered with the planchettes placed in plastic cups, to avoid loss through spillage. During tests, the planchettes were weighed weekly and food replenished when necessary.

Replicate colonies were initiated on consecutive days, with all colonies housed in the stock laboratory under the same conditions of ambient temperature (25° C.), and humidity as during rearing. A control "blank colony", which was identical to a control colony except that no insects were included, was monitored for loss or gain of moisture in the food due to changes in ambient humidity. Any such changes were factored into the calculations of food consumption.

A record was kept of all dead insects, which were counted and sexed weekly when the food was weighed. Dead insects were frozen and stored at −4° C. prior to being subjected to a whole-body uric acid assay. Unless otherwise specified, the total population of each colony was counted every three (3) weeks. When all of the insects, or all of the females, were dead or moribund, the colony was determined to be non-viable and the experiment was terminated. Remaining insects were killed by freezing and stored frozen, as above, to await assaying for uric acid.

Food consumption, in milligrams per individual cockroach (ICmg), was calculated for the first three (3) weeks of the experiment, prior to nymphs hatching. The mean percent change ($\Delta\%$) in population number for each colony was calculated, with the initial number (42) representing 100%. These measurements determined whether the test compositions were ingested, and whether such compositions were effective in inhibiting population growth.

EXAMPLE 2

Uric Acid Assay

Determination of the whole-body uric acid content of the dead cockroaches was conducted essentially according to a standard uricase assay (Cochran (1973) *Comp. Biochem. Physiol.* A46: 409–419). Individual cockroaches, with wings and legs trimmed off, were dried for 24–48 hours at 60° C., weighed, and ground to a fine powder. Uric acid was extracted from the dry tissue with 0.6% aqueous lithium carbonate for three (3) hours at 60° C. with continuous shaking. The extracts were centrifuged to remove tissue debris. After mixing with uricase, the maximum absorption at 292 nm was determined spectrophotometrically, and uric acid concentration was calculated in $\mu$g uric acid/mg of dry tissue.

EXAMPLE 3

Assessment of Xanthine Food Compositions

In two experiments (3a) and (3b), the effects of adding 1% xanthine [Sigma Chemical Co.] to the basic cockroach diet of ground rat chow, were studied. The colonies in each experiment were set up as described in Example I, with the diets being either rat chow alone (RC), or rat chow+1% xanthine (RCX). Each experiment included three replicate colonies for each condition (n=3).

The populations were counted at 6 and 9 weeks (3a) or 10 and 12 weeks (3b), and the percent change in mean population numbers (Δ%) was calculated. Mean individual consumption (ICmg) of the diets for the first three weeks of treatment was calculated from the food-weight data.

The results are shown in Table 1a. The addition of xanthine appeared neither to inhibit feeding nor to adversely affect population growth. In fact, xanthine appeared to enhance reproduction, as population numbers were higher in xanthine-treated colonies than in those fed rat chow alone.

rat chow with oxypurinol [Sigma Chemical Co.] (RC+OXY %) at two concentrations (w/w); and rat chow with 1% xanthine (RCX) and with oxypurinol (+OXY %) at five concentrations (w/w). Mean individual consumption (ICmg), percent change in colony population numbers, and whole-body uric acid concentrations were determined, as previously described.

Mean individual consumption (ICmg) in the first three weeks was calculated, and the results shown in Table 2a below. The addition of oxypurinol alone caused a decrease in food consumption over controls fed untreated food. The addition of xanthine to the diet caused the consumption of oxypurinol-treated food to increase by 35% at 0.1% oxypurinol concentration, and by 56% at the 1.0% oxypurinol concentration.

TABLE 1a

| | EXPERIMENT 3a | | | | EXPERIMENT 3b | | | |
|---|---|---|---|---|---|---|---|---|
| TIME | IC mg (±SEM) | | Δ %(*) | | IC mg (±SEM) | | Δ % | |
| (wks) | RC | RCX | RC | RCX | RC | RCX | RC | RCX |
| 3 | 55.8 (±0.9) | 55.3 (±2.7) | | | 58.0 (±0.4) | 57.9 (±0.8) | | |
| 6 | | | +224% | +278% | | | | |
| 9 | | | +707% | +921% | | | | |
| 10 | | | | | | | +1405% | +1433% |
| 12 | | | | | | | +1774% | +1869% |

(*)+ = increase
Table 1a: Mean individual consumption (IC mg) and percent change (Δ %) in mean population number over time (weeks), in colonies of German cockroaches administered offered food without (RC) or with 1% xanthine (RCX). n = 3

In an additional experiment (3c), German cockroaches from the VPI strain, and colonies of German cockroaches of the Hawthorne strain known to be resistant to insecticides commonly used for cockroach control, were prepared essentially as described in Example 1. The diets administered were either rat chow+1% (w/w) xanthine (RCX), or 50% (w/w) rat chow and bait base+1% xanthine (RCBBX), or bait base+1% xanthine (BBX).

The results are shown in Table 1b. As in experiments 3a and 3b, the addition of xanthine appeared neither to inhibit feeding nor to adversely affect population growth.

TABLE 1b

| TIME | | VPI STRAIN | | | HAWTHORNE STRAIN | | |
|---|---|---|---|---|---|---|---|
| (wks) | TEST | RCX | RCBBX | BBX | RCX | RCBBX | BBX |
| 3 | IC mg (±SEM) | 19 (±1.5) | 23 (±0.9) | 27 (±0.6) | 18 (±0.3) | 22 (±1.7) | 27 (±0.3) |
| 3 | % TOTAL | 27% | 34% | 39% | 27% | 33% | 40% |
| 6 | Δ % | | +441% | | | +933% | |

Table 1b: Mean individual consumption (IC mg) and percent change (Δ %) in mean population numbers over time (weeks), in colonies of German cockroaches of the VPI susceptible strain, and of the Hawthorne resistant strain, offered a choice of diets with 1% xanthine (w/w) in ground rat chow alone (RCX), in ground rat chow and bait base, mixed 50/50 (RCBBX), or in bait base alone (BBX). The ratio of each mixture consumed is given as a percent of the total amount eaten (% TOTAL). (n = 3, 100% = 42)

EXAMPLE 4

Assessment of Xanthine-Oxypurinol Compositions

Colonies of German cockroaches were prepared as described. The diets administered were rat chow alone (RC);

TABLE 2a

| TIME | IC mg (±SEM) XANTHINE 0% | | | IC mg (±SEM) XANTHINE 1% | | | | |
|---|---|---|---|---|---|---|---|---|
| | RC | RC + OXY % | | RC + OXY % | | | | |
| (wks) | RC | 0.1 | 1.0 | 0.1 | 0.5 | 1.0 | 2.0 | 3.0 |
| 3 | 53.7 (±2.0) n = 9* | 36 n = 1 | 32 n = 1 | 48.5 (±1.4) n = 6 | 58.3 (±0.8) n = 3 | 49.9 (±1.9) n = 6 | 52.6 (±1.5) n = 6 | 45.6 n = 1 |

*n = number of colonies
Table 2a: Mean individual consumption (IC mg) of rat chow over three weeks, with or without 1% xanthine, and with various concentrations (w/w) of oxypurinol (OXY %).

The percent changes (Δ%) in mean colony population numbers at 5.5, 6, 7, 9, 10 and 12 weeks of treatment were determined as described, with the results shown in Table 2b below. The addition of oxypurinol alone to the diet did not inhibit population growth. The addition of xanthine plus oxypurinol inhibited population growth to the point of extinction.

TABLE 2b

| TIME | XANTHINE 0% | | | XANTHINE 1% | | | | |
|---|---|---|---|---|---|---|---|---|
| | RC | RC + OXY % | | RC + OXY % | | | | |
| (wks) | CONTROL | 0.1 | 1.0 | 0.1 | 0.5 | 1.0 | 2.0 | 3.0 |
| 5.5 | +690% n = 1 | +460% n = 1 | +1060% n = 1 | | | | | |
| 6 | +126% n = 5 | | | −31% | −50% | −5% | −11% | −55% |
| 9 | +812% n = 5 | | | −92% | −92% | −64% | −77% | −88% |
| 7 | +719% | | | −64% | | −75% | −69% | |
| 10 | +1405% | | | −91% | | −98% | −98% | |
| 12 | +1774% | | | −94% | | −100% | −100% | |

Table 2b: Percent changes (+ or − Δ %) in mean population number, in colonies of German cockroaches offered food with or without 1% xanthine, and with various concentrations (w/w) of oxypurinol (OXY %), over time (weeks). Except where noted, n = 3.

Whole-body uric acid concentrations were calculated from standard uricase assays for cockroaches that died during weeks 5–9 of treatment. Samples from the VPI laboratory strain of German cockroaches also were assayed to show typical "base-line" levels of urates before treatment.

As shown in Table 2c below, females in the VPI strain typically exhibit a slightly higher uric acid level than males, regardless of stage. However, as shown in Tables 2d–2f below, after several weeks of feeding with xanthine and oxypurinol in the diet, there is a marked decline in whole-body urate concentration in all groups regardless of age or sex.

TABLE 2c

| STAGE | GENDER | AGE (wks) | URIC ACID μg/mg (±SEM) |
|---|---|---|---|
| adult | males n = 9 | 6–7 | 1.80 (±0.12) |
| | females n = 10 | | 2.41 (±0.06) |
| nymph | males n = 10 | 5–6 | 2.34 (±0.10) |
| | females | | 2.44 |

TABLE 2c-continued

| STAGE | GENDER | AGE (wks) | URIC ACID μg/mg (±SEM) |
|---|---|---|---|
| | n = 10 | | (±0.22) |
| nymph | males n = 10 | 3–4 | 0.77 (±0.10) |
| | females n = 10 | | 1.51 (±0.10) |

Table 2c: Mean, whole-body uric acid concentrations (μg/mg of dry tissue weight, ±SEM), in different age and gender groups of the VPI laboratory strain of German cockroaches that are typical of those used in the feeding experiments.

TABLE 2d

| TIME | | RCX + OXY % | | |
|---|---|---|---|---|
| (wks) | RC | 0.1 | 1.0 | 2.0 |
| 5 | 2.42 (±0.12) n = 5 | 0.54 (±0.05) n = 25 | 0.32 (±0.06) n = 17 | 0.31 (±0.05) n = 17 |

TABLE 2d-continued

| TIME | | RCX + OXY % | | |
|---|---|---|---|---|
| (wks) | RC | 0.1 | 1.0 | 2.0 |
| 6 | 2.79 | 0.43 | 0.30 | 0.27 |
|  | (±0.21) | (±0.04) | (±0.04) | (±0.03) |
|  | n = 4 | n = 32 | n = 35 | n = 26 |
| 7 | 2.78 | 0.54 | 0.25 | 0.21 |
|  | (±0.25) | (±0.10) | (±0.04) | (±0.04) |
|  | n = 6 | n = 8 | n = 14 | n = 12 |
| 9 | 3.16 | 0.51 | 0.14 | 0.32 |
|  | (±0.06) | n = 1 | (±0.04) | (±0.10) |
|  | n = 10 |  | n = 7 | n = 3 |

Table 2d: Mean whole-body uric acid concentrations ($\mu$g/mg dry tissue weight ±SEM) in male German cockroaches on food without (RC), or with, 1% xanthine (RCX) and various percent concentrations (w/w) of oxypurinol (OXY %).

TABLE 2e

| TIME | | RCX + OXY % | | |
|---|---|---|---|---|
| (wks) | RC | 0.1 | 1.0 | 2.0 |
| 5 | 2.63 | 0.31 | 0.31 | 0.28 |
|  | (±0.14) | (±0.13) | (±0.04) | (±0.08) |
|  | n = 3 | n = 6 | n = 8 | n = 7 |
| 6 | 3.13 | 0.31 | 0.34 | 0.35 |
|  | (±0.04) | (±0.03) | (±0.06) | (±0.06) |
|  | n = 4 | n = 27 | n = 27 | n = 18 |
| 7 | 2.95 | 0.43 | 0.22 | 0.26 |
|  | (±0.18) | (±0.04) | (±0.04) | (±0.06) |
|  | n = 4 | n = 24 | n = 23 | n = 14 |
| 9 | 3.14 | 0.21 | 0.29 | 0.34 |
|  | n = 1 | (±0.03) | (±0.04) | (±0.05) |
|  |  | n = 21 | n = 14 | n = 13 |

Table 2e: Mean whole-body uric acid concentrations ($\mu$g/mg dry tissue weight ±SEM) in female German cockroaches on food without (RC), or with, 1% xanthine (RCX) and various percent concentrations (w/w) of oxypurinol (OXY %).

TABLE 2f

| TIME | | RCX + OXY % | | |
|---|---|---|---|---|
| (wks) | RC | 0.1 | 1.0 | 2.0 |
| 5 | 1.95 | 0.53 | 0.32 |  |
|  | (±0.36) | (±0.04) | (±0.18) |  |
|  | n = 4 | n = 3 | n = 2 |  |
| 6 | 2.95 |  |  | 0.08 |
|  | (±0.09) |  |  | (±0.06) |
|  | n = 5 |  |  | n = 2 |
| 7 | 3.14 |  |  | 0.13 |
|  | (±0.03) |  |  | (±0.08) |
|  | n = 4 |  |  | n = 2 |

TABLE 2f-continued

| TIME | | RCX + OXY % | | |
|---|---|---|---|---|
| (wks) | RC | 0.1 | 1.0 | 2.0 |
| 9 | 3.26 |  |  | 0.14 |
|  | n = 1 |  |  | n = 1 |

Table 2f: Mean whole-body uric acid concentrations ($\mu$g/mg dry tissue weight ±SEM) in German cockroach nymphs offered food without (RC), or with, 1% xanthine (RCX) and various percent concentrations (w/w) of oxypurinol (OXY %).

In additional experiments, replicate colonies were prepared essentially as described in Example 1. The diets adminstered were rat chow+bait base alone (RCBB); rat chow+bait base+1% xanthine (RCBBX) and oxypurinol (OXY) at two concentrations; and bait base+1% xanthine (BBX) and oxypurinol (OXY) at two concentrations.

Mean individual consumption (ICmg) and percent change ($\Delta$%) in mean population number were determined over time (weeks). The results are shown in Table 2g below.

TABLE 2g

| | | CONTROL | 1% OXY | | 2% OXY | |
|---|---|---|---|---|---|---|
| TIME | TEST | RCBB | RCBBX | BBX | RCBBX | BBX |
| 3 | IC mg | 64 | 50 | 41 | 47 | 42 |
|  | (±SEM) | (±1.6) | (±1.3) | (±1.5) | (±3.5) | (±1.3) |
| 3 | $\Delta$ % | −10% | −14% | −64% | −36% | −69% |
| 6 | $\Delta$ % | +798% | −94% | −100% | −96% | −100% |

Table 2g: Mean individual consumption (IC mg), and percent changes ($\Delta$ %) in mean population number over time (weeks), in colonies of German cockroaches of the VPI susceptible strain offered diets without xanthine or diets with 1% xanthine (X), and 1% or 2% oxypurinol (OXY). The foods were rat chow and bait base 50/50 (RCBB), or bait base alone (BB). (n = 3; 100% = 42)

A rapid population decline and extinction was observed in the treated colonies, compared with the untreated controls. Although the mean individual consumption was slightly lower in those colonies administered treated bait-base compositions, deleterious effects occurred more rapidly than in colonies administered treated rat chow (Table 2b). In the present experiment, the amounts of oxypurinol ingested in the first three weeks were 500 $\mu$g and 410 $\mu$g in the respective foods at 1% oxypurinol, and 940 $\mu$g and 840 $\mu$g respectively, at 2% oxypurinol.

In yet further experiments, replicate colonies of German cockroaches were prepared essentially as described in Example 1. The diets administered were rat chow alone (RC); bait base alone (BB); bait base+xanthine (BBX) and two concentrations of oxypurinol (OXY); rat chow+ xanthine at three concentrations (RCX) and oxypurinol (OXY) at three concentrations.

The results are shown in Table 2h below.

TABLE 2h

| TIME | | RC OR BB | BBX 0.5% | | RCX 1% | RCX 2% | RCX 3% |
|---|---|---|---|---|---|---|---|
| (wks) | TEST | CONTROLS | OXY .5% | OXY 1% | OXY .5% | OXY 2% | OXY 3% |
| 3 | IC mg | 49 | 29 | 33 | 58 | 47 | 45 |
|  | (±SEM) | (±1.2) | (±0.3) | (±0.7) | (±0.8) | (±1.1) | (±0.3) |
| 3 | $\Delta$ % | −4% | −32% | −50% | −12% | −11% | −21% |

TABLE 2h-continued

| TIME (wks) | TEST | RC OR BB CONTROLS | BBX 0.5% OXY .5% | OXY 1% | RCX 1% OXY .5% | RCX 2% OXY 2% | RCX 3% OXY 3% |
|---|---|---|---|---|---|---|---|
| 6 | Δ % | +213% | −96% | −82% | −48% | −50% | −50% |
| 9 | Δ % | +722% | −100% | −99% | −92% | −88% | −86% |

Table 2h: Mean individual consumption (IC mg) and percent change (Δ %) in mean population number over time (weeks) in colonies of German cockroaches of the VPI susceptible strain administered either untreated rat chow (RC) or bait base (BB), or these foods treated with various concentrations (w/w) of xanthine (X) ranging from 0.5% to 3%, and with various concentrations (w/w) of oxypurinol ranging from 0.5% to 3%. (n = 5 untreated, n = 3 treated, 100% = 42)

As illustrated in Table 2h, population control was achieved in all of the treated colonies. However, the rate of population decline was slowest in the colonies fed the higher concentrations of xanthine and oxypurinol (2% and 3%), although mean individual consumption for these groups matched those of the untreated controls. The fastest declines in population were observed in those colonies with the lowest consumption rate and which had been administered diets containing 0.5% xanthine and either 0.5% or 1.0% oxypurinol in a bait-base composition. Highest consumption was observed in colonies administered a diet of 1% xanthine and 0.5% oxypurinol, with reduction in population moderate as to time. The amount of oxypurinol and xanthine ingested individually ranged from 145 $\mu$g to 1,350 $\mu$g over the first three weeks in these trials.

EXAMPLE 5

Assessment of Xanthine-Oxypurinol Compositions Offered for Different Durations

Colonies were prepared essentially as described in Example 1. The diets administered were rat chow alone (RC) and rat chow+1% xanthine (RCX) plus oxypurinol (OXY) at three concentrations. The food was offered for durations of either 24 hours, or 1, 2, or 3 weeks. At the end of the treatment time, the treated food was removed, and the insects were offered untreated rat chow for the remainder of the test As shown in Table 3a below, a minimum dose of oxypurinol must be ingested over time to achieve population inhibition. For example, the 24-hour treatment affected population numbers when compared with the control, but did not control population numbers at any concentration of oxypurinol. Calcation revealed that the individual consumption of oxypurinol ingested during this time ranged from 6 $\mu$g to 104 $\mu$g.

TABLE 3a

| TREATMENT DURATION | TIME (wks) | RC | RCX + OXY % | | |
|---|---|---|---|---|---|
| | | | 0.1 | 1.0 | 2.0 |
| 24 hours | 6 | +500% | +250% | +114% | +109% |
| 1 week | 6 | +887% | +137% | −45% | −49% |
| | 9 | +1157% | +320% | −63% | −57% |
| | 12 | +1580% | +853% | −5% | −31% |
| 2 weeks | 9 | +591% | +36% | −65% | −90% |
| | 12 | +750% | +213% | −66% | −94% |
| | 15 | >+750% | +561% | −45% | −96% |

TABLE 3a-continued

| TREATMENT DURATION | TIME (wks) | RC | RCX + OXY % | | |
|---|---|---|---|---|---|
| | | | 0.1 | 1.0 | 2.0 |
| 3 weeks | 6 | +391% | −58% | −71% | −92% |
| | 9 | +1050% | −71% | −92% | −97% |
| | 12 | +1604% | −79% | −96% | −98% |

Table 3a: Percent change (+ or −) in mean population numbers in colonies fed a diet of rat chow alone (RC), or rat chow combined with 1% xanthine (RCX), and with various concentrations (w/w) of oxypurinol (OXY %). Duration of treatments was 24 hrs, or 1, 2, or 3 weeks, after which rat chow alone was offered. n = 3.

Treatment with 0.1% oxypurinol for one or two weeks also resulted in lower population numbers when compared with controls, and delayed egg-hatch by 1–2 weeks, but the treated colonies were recovering when they were terminated at 12 weeks. However, three (3) weeks of treatment at 0.1% oxypurinol did cause a substantial reduction in population numbers in the weeks following treatment, with no recovery noted by 12 weeks, and with only one viable egg case, which hatched six weeks later than normal.

Colonies treated for two (2) weeks with 2% oxypurinol, or for three (3) weeks with 1% or 2% oxypurinol did not recover, even when the "recovery" time was extended to fifteen (15) weeks. Mean individual consumption of oxypurinol was 734 $\mu$g, 579 $\mu$g, and 1,140 $\mu$g respectively.

Additional experiments were conducted with colonies of German cockroaches of the American Cyanamid (AMCY) susceptible strain, prepared essentially as described in Example 1. The diets administered were bait base alone (BB) or bait base+1% xanthine and 1% oxypurinol. The food was offered for durations of either 3, 6, 9, 12, or 15 days. At the end of the treatment time, the treated food was removed, and the insects were offered untreated bait base (BB) for the remainder of the test period. The controls were offered either untreated bait base (BB) continuously, or treated food continuously, until the end of the trial.

As shown in Table 3b below, treatment for 6 days or more was required to achieve irreversible decline in the test population.

TABLE 3b

| TREATMENT DURATION | TIME (wks) | BB | BBX + 1% OXY |
|---|---|---|---|
| 3 DAYS | 3 | −2% | −8% |
| | 6 | —* | −27% |
| | 9 | +1910% | 0% |
| 6 DAYS | 3 | −2% | −10% |
| | 6 | — | −53% |

TABLE 3b-continued

| TREATMENT DURATION | TIME (wks) | BB | BBX + 1% OXY |
|---|---|---|---|
| | 9 | +1588% | −2% |
| 9 DAYS | 3 | 0% | −13% |
| | 6 | — | −75% |
| | 9 | +1452% | −90% |
| 12 DAYS | 3 | 0% | −25% |

TABLE 3b-continued

| TREATMENT DURATION | TIME (wks) | BB | BBX + 1% OXY |
|---|---|---|---|
| | 6 | — | −89% |
| | 9 | +1719% | −96% |
| 15 DAYS | 3 | 0% | −17% |
| | 6 | — | −90% |
| | 9 | +1781% | −98% |
| CONTINUOUS TREATMENT | 3 | — | −2% |
| | 6 | — | −100% |

Table 3b: Percent change (Δ %) in mean population numbers over time (weeks) in colonies of German cockroaches of the AMCY susceptible strain fed a diet of bait base alone (BB), or bait base + 1% xanthine and 1% oxypurinol. Duration of treatment was 3, 6, 9, 12, or 15 days, after which untreated base bait was administered. * = no data recorded. (n = 3, 100% = 42)

Individual consumption of oxypurinol for treatment durations of 3 days, 6 days, 9 days, 12 days, 15 days, and continuously, was 64 μg, 150 μg, 193 μg, 265 μg, 301 μg, and 434 μg, respectively.

EXAMPLE 6

Assessment of Food Choice

Colonies were prepared essentially as described in Example 1, with three replicates of each condition. Planchettes containing either untreated food (RC) or food treated with xanthine+oxypurinol (RCX+OXY%) were offered together in each colony. Food weights for each planchette were calculated to determine how much of each was consumed. The treatments consisted of rat chow with 1% xanthine and oxypurinol at either 0.1%, 0.5% or 1.0% (w/w) concentration. The control colony was given two planchettes of untreated rat chow.

The results, as shown in Table 4a below, indicate that the insects consumed either the same quantity of treated and untreated food (at 0.5% oxypurinol), or ate more of the treated than the untreated food (at 0.1% and 2.0% oxypurinol). The range of oxypurinol ingested was calculated to be between 29 μg and 265 μg per individual over the first three weeks, and a high level of population-growth control was achieved, especially at 1.0% oxypurinol concentration.

TABLE 4a

| TIME (wks) | TEST | RC CONTROL | RC | RCX + OXY % 0.1 | RC | RCX + OXY % 0.5 | RC | RCX + OXY % 1.0 |
|---|---|---|---|---|---|---|---|---|
| 3 | IC mg | 58.9 | 23.1 | 29.4 | 25.7 | 25.6 | 24.7 | 26.5 |
| | ±SEM | ±1.7 | ±3.1 | ±0.30 | ±1.0 | ±1.3 | ±0.9 | ±2.0 |
| | IC μg OXY | 0 | 0 | 29.4 | 0 | 128 | 0 | 265 |
| | % TOTAL | 100% | 43% | 57% | 50% | 50% | 48% | 52% |
| 7 | Δ % | +422% | −64% | | −72% | | −83% | |
| 9 | Δ % | +1378% | −71% | | −80% | | −94% | |
| 12 | Δ % | +2007% | −76% | | −71% | | −96% | |

Table 4a: Mean individual consumption (IC mg) and percent change in mean population numbers (Δ %) over time (weeks), in colonies where treated (RCX + OXY %) and untreated (RC) food were offered together as a choice of diet. The amount of oxypurinol ingested over the first three weeks is shown as μg/individual (IC μg OXY), and the ratio of treated and untreated food consumed is given as a percent of the total amount eaten (% TOTAL). (n = 3; 100% = 42)

In additional experiments, replicate colonies were prepared essentially as described in Example 1. Planchettes containing either untreated bait base (BB), or bait base+1% xanthine (BBX) and either 1% or 2% oxypurinol (OXY), were offered together in each colony. Results were compared with control colonies offered only untreated bait base.

The results, as shown in Table 4b below, demonstrate that adding a combination of xanthine and either 1% or 2% oxypurinol to the inert bait base caused the population to diminish to the point of extinction. This occurred even though the insects had untreated food available to them as well. There was little, or no, feeding inhibition exhibited with these compounds added to the food.

TABLE 4b

| TIME (wks) | TEST | BB CONTROL | BB | BBX 1% OXY | BB | BBX 2% OXY |
|---|---|---|---|---|---|---|
| 3 | IC mg (±SEM) | 61 n = 1 | 14 (±0.3) | 25 (±0.6) | 21 (±1.4) | 16 (±1.4) |
| 3 | % TOTAL | 100% | 36% | 64% | 57% | 43% |
| 3 | Δ % | −2% | −57% | | −60% | |
| 4 | Δ % | −2% | −93% | | −87% | |
| 6 | Δ % | +369% | −98% | | −99% | |

Table 4b: Mean individual consumption (IC mg), and percent change (Δ %) in mean population number over time (weeks), in colonies of German cockroaches, where untreated bait base (BB), and bait base treated (w/w) with 1% xanthine (BBX) and either 1% or 2% oxypurinol (OXY), were offered as a choice of food. (n = 3, 100% = 42)

The range of oxypurinol ingested was calculated to be between 250 μg–320 μg per individual insect over the first three weeks of treatment.

EXAMPLE 7

Life Stage Effects of Xanthine-oxypurinol Compositions

Colonies of German cockroaches were housed as previously described in Example 1, with the usually mixed stages separated into three different colonies. Colonies consisted of either newly-molted adults (five males and five females, 6–7 weeks old); large nymphs (eight males and eight females, 5–6 weeks old); or small nymphs (eight males and eight females, 3–4 weeks old). Colonies of older adults (five males and five females, 7–8 weeks old) also were tested.

The diets administered were either rat chow alone (RC), or rat chow+1% xanthine (RCX) plus various concentrations (w/w) of oxypurinol (OXY %). Mean individual consumption (ICmg) and percent change in mean population number (Δ%) were determined for each stage, and are shown in Tables 5a through 5d below, for adults, large nymphs, small nymphs, and older adults, respectively.

The data in these tables confirm that the primary impact of treatment with xanthine plus oxypurinol occurs as the cockroaches attempt to reproduce. The effect is probably caused by depletion of the insects' metabolic reserves, including uric acid stores which cannot be replaced because of irreversible enzyme inhibition. However, very small nymphs which hatch in a dying colony also are affected in that they are usually too weak to survive, and rarely reach their second instar. It is probable that they are not invested with the metabolic reserves that are normally passed to them prenatally. Their continued feeding on treated food also prevents the young nymphs from developing their own metabolic stores, especially stores of uric acid.

Adult males were observed to be the first to die. At mating, adult males utilize a large part of their reserves to pass urates as well as mature sperm to the females. Females who have just produced an egg-case, which necessitates a large investment of nutritional reserves, die shortly thereafter, usually with the non-viable egg-case protruding from the ovipositor.

Cochran observed that cyclic feeding occurs in adult females in relation to egg production (Cochran (1983) *Entomol. Exp. Appl.* 34: 51–57). In this oothecal cycle, the females feed vigorously while maturing the oocytes, and sparingly while carrying an egg-case. These phenomena would account for the high feeding rates and early mortality of the newly-emerged adults (Table 5a), as well as the low feeding rates of the older adults (Table 5d). These latter females were likely to already have matured the eggs that would fill oothecae soon after the colony was assembled, and thus were in the low feeding-rate part of their cycle. Their first nymphal hatch would account for the precipitous rise in population numbers in these colonies (Table 5d), followed by the gradual weakening of the colonies as the adults attempted to reproduce further and the newly-hatched nymphs died.

Nymphs followed the same pattern of mortality as the adults, and were most affected by the treated diet after molting to the adult stage, when they normally feed vigorously in preparation for maturing their first oocytes. The delay in the rate at which the population declined in the large nymph colony (Table 5b), and small nymph colony (Table 5c), is further evidence that the major impact occurs during reproduction. This would have happened between weeks 9–11 of the experiment for these age-groups.

The effective dosage range for oxypurinol with xanthine is very wide in these experiments, causing high mortality at 99.5 μg/individual measured over three weeks in the newly-molted adults (Table 5a), and slower control at higher individual consumption rates when the colonies were started as nymphs. However, it is clear that, although there is a different effect on the cockroaches depending on their age when treatment is started, they are all affected as they attempt to reproduce.

TABLE 5a

| | COLONY STARTED AS ADULTS (n = 1) | | | |
|---|---|---|---|---|
| TIME | | | RCX + OXY % | |
| wks | TEST | RC | 0.1 | 1.0 | 2.0 |
| 3 | IC mg | 87.0 | 99.5 | 76.8 | 84.8 |
| 3 | IC μg OXY | 0 | 99.5 | 768 | 1696 |
| 6 | Δ % | +1430% | −94% | −75% | −88% |
| 9 | Δ % | +1310% | −100% | −90% | −100% |
| 12 | Δ % | +1810% | −100% | −100% | −100% |

Table 5a: Mean individual consumption (IC mg) and percent change in mean population number (Δ %) in colonies of newly-molted adult German cockroaches fed untreated rat chow (RC) or rat chow + 1% xanthine (RCX) and various concentrations (w/w) of oxypurinol (OXY %).

TABLE 5b

| | COLONY STARTED AS LARGE NYMPHS (n = 1) | | | |
|---|---|---|---|---|
| TIME | | | RCX + OXY % | |
| wks | TEST | RC | 0.1 | 1.0 | 2.0 |
| 3 | IC mg | 82.8 | 76.9 | 65.3 | 79.3 |
| 3 | IC μg OXY | 0 | 76.9 | 653 | 1586 |
| 6 | Δ % | −6% | −50% | −31% | −6% |
| 9 | Δ % | +1613% | −69% | −81% | −63% |
| 12 | Δ % | +1800% | −88% | −100% | −100% |

Table 5b: Mean individual consumption (IC mg) and percent change in mean population number (Δ %) in colonies of large German cockroach nymphs (5–6 weeks old at the starting date) fed untreated rat chow (RC) or rat chow + 1% xanthine (RCX) and various concentrations (w/w) of oxypurinol (OXY %).

TABLE 5c

| | COLONY STARTED AS SMALL NYMPHS (n = 1) | | | |
|---|---|---|---|---|
| TIME | | | RCX + OXY % | |
| wks | TEST | RC | 0.1 | 1.0 | 2.0 |
| 3 | IC mg | 54.9 | 53.9 | 52.4 | 40.4 |
| 3 | IC μg OXY | 0 | 53.9 | 524 | 808 |
| 6 | Δ% | −50% | −31% | −19% | −81% |
| 9 | Δ% | +719% | −69% | −81% | −88% |
| 12 | Δ% | +775% | −88% | −100% | −100% |

Table 5c: Mean individual consumption (IC mg) and percent change in mean population number (Δ%) of small German Cockroach nymphs (3–4 weeks old at the starting date) fed untreated rat chow (RC) or rat chow + 1% xanthine (RCX) and various concentrations (w/w) of oxypurinol (OXY %).

TABLE 5d

| | COLONY STARTED AS OLDER ADULTS (n = 3) | | | |
|---|---|---|---|---|
| TIME | | | RCX + OXY % | |
| wks | TEST | RC | 0.1 | 1.0 | 2.0 |
| 3 | IC mg (±SEM) | 38.7 | 37.2 (±1.9) | 35.0 (±0.6) | 35.2 (±1.8) |
| 3 | IC μg OXY | 0 | 37.2 | 350 | 704 |
| 6 | Δ% | +1150% | +557% | +403% | +823% |

TABLE 5d-continued

COLONY STARTED AS OLDER ADULTS (n = 3)

| TIME | | | RCX + OXY % | | |
|---|---|---|---|---|---|
| wks | TEST | RC | 0.1 | 1.0 | 2.0 |
| 9 | Δ% | +1030% | +33% | +40% | −197% |
| 12 | Δ% | +1820% | −73% | −67% | −30% |

Table 5d: Mean individual consumption (IC mg) and percent change in mean population number (Δ%) in colonies of older German cockroach adults (8–9 weeks old at the starting date) fed untreated rat chow (RC) or rat chow + 1% xanthine (RCX) and various concentrations (w/w) of oxypurinol (OXY %).

EXAMPLE 8

Assessment of Compositions Containing Trimethoprim

Replicate colonies of German cockroaches were prepared essentially as described in Example 1. The diets adminstered were either rat chow alone (RC); rat chow with various concentrations (w/w) of trimethoprim (RC+T %), or rat chow+1% xanthine (RCX) and various concentrations (w/w) of trimethoprim (T %).

As shown in Table 6a below, the addition of trimethoprim alone did not inhibit population growth, although there was some eventual weakening of the treated colonies. As shown in Table 6b below, however, the combination of xanthine and trimethoprim caused rapid inhibition of population growth.

TABLE 6a

| TIME | | | RC + T % | | |
|---|---|---|---|---|---|
| WKS | TEST | RC | 0.5 | 1.0 | 2.0 |
| 3 | IC mg | 62 | 61 | 58 | 54 |
|  | (±SEM) | (±2.2) | (±3.5) | (±3.4) | (±1.7) |
| 12 | Δ% | +1398% | +1246% | +1013% | +384% |

Table 6a: Mean individual consumption (IC mg) of rat chow without (RC) or with various concentrations (w/w) of trimethoprim (RC + T %), over time (weeks), shown in conjunction with percent change in mean population number (Δ%), in colonies of German cockroaches where the starting number (42) = 100%. n = 5

TABLE 6b

| | | | RCX + T % | | |
|---|---|---|---|---|---|
| TIME | | RC | 1.0 | 2.0 | 3.0 |
| wks | TEST | n = 6 | n = 3 | n = 12 | n = 3 |
| 1 | IC mg | 17.3 | 12.0 | 8.8 | 5.8 |
|  | (±SEM) | (±2.4) | (±0.9) | (±0.7) | (±0.1) |
|  | Δ% | −1% | −4% | −28% | −41% |
| 3 | IC mg | 44.7 | 33.9 | 22.6 | 13.4 |
|  | (±SEM) | (±2.1) | (±1.1) | (±2.8) | (±1.3) |
|  | Δ% | −16% | −23% | −77% | −98% |
| 6 | Δ% | +36% | −44% | −67% | −98% |

Table 6b: Mean individual consumption (IC mg), and percent change in mean population number (Δ%), over time (weeks), in colonies of German cockroaches offered food without xanthine (RC) or with 1% xanthine (RCX) and various concentrations (w/w) of trimethoprim (T %), where the colony starting number (42) = 100%.

Whole-body uric acid concentrations were calculated from standard uricase assays, as previously described. As shown in Table 6c below, uric acid metabolism was not affected by treatment with a combination of xanthine and trimethoprim. During the first three-weeks, there was a mean Δ% of −82% of the populations in the treated colonies, with 65% of these still nymphs when they died. This represents 72% of the nymphs used for the experiment, and confirms that effects are most pronounced during nymphal molt.

TABLE 6c

| WEEK | GROUP | RC | RCX + 2% T |
|---|---|---|---|
| 3–4 | males | 2.04 | 2.61 |
|  |  | ±0.12 | ±0.05 |
|  |  | n = 19 | n = 9 |
|  | females | 2.54 | 2.64 |
|  |  | ±0.06 | ±0.03 |
|  |  | n = 17 | n = 3 |
|  | nymphs | 2.76 | 2.62 |
|  |  |  | ±0.12 |
|  |  | n = 1 | n = 9 |

Table 6c: Mean whole-body uric acid concentrations (μg/mg dry tissue weight ±SEM), in three groups of German cockroaches offered untreated food (RC), or food treated with 1% xanthine (RCX) and 2% trimethoprim (w/w).

In additional experiments, replicate colonies of cockroaches were prepared essentially as described in Example 1. The diets administered were untreated 50/50 rat chow+bait base (w/w) (RCBB); rat chow+bait base+1% xanthine (RCBBX) and 2% trimethoprim (T); bait base+1% xanthine (BBX) and 2% trimethoprim (T). Mean individual consumption (ICmg) over the first three weeks and the percent change (Δ%) in mean population number over time were calculated as before.

As shown in Table 6d below, consumption of the untreated food was much higher than consumption of the treated food, regardless of composition, indicating that the insects found compositions with trimethoprim, distasteful. However, both of the treated populations lost nymphs early in the trial, and the colonies declined to extinction over nine weeks of treatment. The rate of ingestion of trimethoprim was 680 μg to 700 μg over the first three weeks.

TABLE 6d

| TIME (wks) | TEST | RCBB CONTROL | RCBBX 2% T | BBX 2% T |
|---|---|---|---|---|
| 3 | IC mg | 68 | 34 | 35 |
|  | (±SEM) | (±1.7) | (±3.0) | (±4.6) |
| 3 | Δ% | −5% | −79% | −72% |
| 6 | Δ% | +782% | −79% | −92% |
| 9 | Δ% | +1130% | −81% | −99% |

Table 6d: Mean individual consumption (IC mg) and percent change (Δ%) in mean population numbers over time (weeks) in colonies of German cockroaches of the VPI susceptible strain offered foods with or without 1% xanthine (X) and 2% trimethoprim (T). The foods were 50% rat chow with bait base (RCBB), or bait base alone (BB). (n = 3, 100% = 42)

To test the effects of a higher concentration of xanthine with trimethoprim, colonies were prepared essentially as described in Example 1. The diets administered were either untreated rat chow (RC) or rat chow +2% xanthine (X) and 2% trimethoprim (T). Calculations were done as previously described As shown in Table 6e below, the higher concentration of xanthine did not change the feeding pattern when administered with trimethoprim, though the decline of the population was faster, with extinction observed at about six weeks. The ingestion rate of trimethoprim was about 640 μg over three weeks.

TABLE 6e

| TIME (wks) | TEST | RC CONTROL | RCXT |
|---|---|---|---|
| 3 | IC mg (±SEM) | 62 n = 1 | 32 (±1.5) |
| 3 | Δ% | −9% | −90% |
| 6 | Δ% | +1262% | −98% |

Table 6e: Mean individual consumption (IC mg) and percent change (Δ%) in mean population number over time (weeks), in colonies of German cockroaches of the VPI susceptible strain, offered food without (RC) or with 2% xanthine and 2% trimethoprim (T) (w/w). (n =3; 100% = 42)

To further determine the effects of different concentrations of xanthine and trimethoprim in compositions, especially with regard to body size, additional tests were conducted using the large cockroach *Periplaneta americana*—the American cockroach. Three colonies were prepared, each consisting of last-instar nymphs, of which ten were females, and five were males. The diets administered with either untreated rat chow (RC) or rat chow treated+1% xanthine and either 2% or 5% trimethoprim.

Although considerable feeding inhibition occurred with the 5% trimethoprim composition, the population was controlled for 32 weeks, at which time only 15 nymphs hatched. This was in marked contrast to the control colony, where an average 47.4 nymphs per female were hatched. It appears that higher concentrations of trimethoprim, with the compound microencapsulated to mask its presence, would achieve complete control.

EXAMPLE 9

Treatment of Resistant Cockroaches with Xanthine-Oxypurinol Compositions

Colonies of cockroaches were prepared essentially as described in Example 1, except that the insects were taken from laboratory stocks of two German cockroach strains that are known to be resistant to insecticides commonly used for cockroach control. The two strains were: (A) the Hawthorne strain, and (B) the Las Palms strain. Profiles of the resistance ratios exhibited by these two strains are shown in Table 7a below.

TABLE 7a

| INSECTICIDE | HAWTHORNE RR | LAS PALMS |
|---|---|---|
| ORGANOPHOSPHATES | | |
| Diazinon | 2.0 | >75 |
| Chlorpyrifos | 10.8 | >50 |
| Acephate | 2.0 | 1.2 |
| Malathion | 5.5 | >50 |
| CARBAMATES | | |
| Propoxur | 1.7 | >60 |
| Bendiocarb | 2.2 | >70 |
| PYRETHROIDS | | |
| Pyrethrins | >140 | >140 |
| Allethrin | >140 | >140 |
| Permethrin | 0.5 | 3.2 |
| Phenothrin | 0.6 | >120 |
| Fenvalerate | 0.9 | >60 |
| Esfenvalerate | 0.8 | 7.0 |
| Cyfluthrin | 1.8 | 2.5 |
| Cypermethrin | 1.6 | >80 |

TABLE 7a-continued

| INSECTICIDE | HAWTHORNE RR | LAS PALMS |
|---|---|---|
| BIO-CHEMICAL | | |
| Avermectin | 2.4 | 1.5 |

Table 7a: Resistance ratio (RR) profiles for the Hawthorne and Las Palms resistant strains, where, on a continuum of rising resistance, RR >2.0 indicates that resistance is developing, and RR >3.0 indicates that the gene frequency for resistance has increased. RR is calculated as (Test strain $LT_{50}$) ÷ (Susceptible strain $LT_{50}$), where $LT_{50}$ is the time it takes for the intoxicant to achieve 50% mortality in a treated population.

Mean individual consumption (ICmg) in the first three-weeks was calculated as previously described. As shown in Tables 7b and 7c below, ICmg for both strains was consistent across all concentrations of the food mixtures. The Hawthorne strain exhibited a maximum decrease in consumption of 22% for a diet containing 3% oxypurinol. This represents a dose of 1,260 μg of oxypurinol over the first three weeks.

TABLE 7b

| TIME (wks) | RC | RCX + OXY % | | | |
|---|---|---|---|---|---|
| | | 0.1 | 1.0 | 2.0 | 3.0 |
| HAWTHORNE STRAIN | | | | | |
| 3 | 53.6 (±3.5) n = 4 | 47.1 (±0.6) n = 3 | 48.0 (±1.3) n = 3 | 47.1 (±0.8) n = 3 | 42.0 (±0.4) n = 4 |
| LAS PALMS STRAIN | | | | | |
| 3 | 45.2 (±1.3) n = 4 | 39.5 (±1.0) n = 3 | 40.0 (±0.4) n = 3 | 40.0 (±2.3) n = 3 | 40.3 (±0.5) n = 4 |

Table 7b: Mean individual consumption (IC mg), over time (wks), of rat chow offered without (RC), or with 1% xanthine (RCX), and with various concentrations (w/w) of oxypurinol (OXY %), by German cockroaches of the Hawthorne and Las palms resistant strains.

The effect of xanthine-oxypurinol combinations on population growth was determined as previously described. As shown in Tables 7c and 7d below, the combination controlled the population growth of both resistant strains. This indicates that the mode of action of the xanthine-oxypurinol combination is not affected by the multiple resistance mechanisms present in these strains.

TABLE 7c

| TIME (wks) | RC | RCX + OXY % | | | |
|---|---|---|---|---|---|
| | | 0.1 | 1.0 | 2.0 | 3.0 |
| 6 | +438% | −32% | −22% | +12% | −21% |
| 9 | +997% | −55% | −59% | −38% | −67% |
| 12 | +1,601% | −77% | −78% | −76% | −98% |

Table 7c: Percent changes (+ or −) in mean population number in colonies of German cockroaches of the Hawthorne resistant strain, offered food without (RC) or with 1% xanthine (RCX), and with various concentrations (w/w) of oxypurinol (OXY %), over time (weeks). n = 3.

TABLE 7d

| TIME | | RCX + OXY % | | | |
|------|------|------|------|------|------|
| wks | RC | 0.1 | 1.0 | 2.0 | 3.0 |
| 6 | +146% | +50% | +68% | +31% | −25% |
| 9 | +1,074% | −50% | −8% | −60% | −70% |
| 12 | +1,624% | −78% | −67% | −88% | −95% |

Table 7d: Percent changes (+ or −) in mean population number in colonies of German cockroaches of the Las Palms resistant strain, offered food without (RC) or with 1% xanthine (RCX), and with various concentrations (w/w) of oxypurinol, over time (weeks). n = 3.

Additional experiments were conducted to assess compositions of xanthine with higher concentrations of oxypurinol. Colonies of cockroaches were prepared as described, using the Hawthorne and Las Palms resistant strains. The diets administered were untreated rat chow (RC) or rat chow treated+1% xanthine and four concentrations of oxypurinol.

As shown in Tables 7e and 7f below, there was little difference in mean individual consumption (ICmg) over the first three weeks in either strain. A gradual decline in mean population over time (weeks) was observed, with extinction at 12 weeks for the Hawthorne strain. A slightly slower rate of decline was observed in the Las Palms strain. At 5% concentration, ingestion of oxypurinol was 2,350 μg for both strains, and population decline was equivalent. At the other concentrations, the range of oxypurinol ingested was 920 μg–1,840 μg (2%–4%) for the Hawthorne strain, and 960 μg–1,960 μg (2%–4%) for the Las Palms strain.

TABLE 7e

| TIME | | RC | RCX + OXY | | | |
|------|------|------|------|------|------|------|
| (WKS) | TEST | CONTROL | 2% | 3% | 4% | 5% |
| 3 | IC mg | 49 | 46 | 45 | 46 | 47 |
|   | (±SEM) | (±2.8) | (±3.5) | (±3.2) | (±3.2) | (±3.7) |
| 6 | Δ% | +386% | −62% | −66% | −29% | −56% |
| 9 | Δ% | +1316% | −89% | −91% | −75% | −89% |
| 12 | Δ% | +1642% | −100% | −100% | −100% | −100% |

Table 7e: Mean individual consumption (IC mg) and percent change (Δ%) in mean population number over time (weeks) in colonies of German cockroaches of the Hawthorne resistant strain, offered food without (RC) or with (w/w) 1% xanthine and various concentrations of oxypurinol (OXY). (n = 3; 100% = 42)

TABLE 7f

| TIME | | RC | RCX + OXY | | | |
|------|------|------|------|------|------|------|
| (WKS) | TEST | CONTROL | 2% | 3% | 4% | 5% |
| 3 | IC mg | 48 | 48 | 49 | 49 | 47 |
|   | (±SEM) | (+1.5) | (±2.3) | (±2.6) | (±1.9) | (±2.0) |
| 6 | Δ% | +271% | −13% | −40% | −48% | −48% |
| 9 | Δ% | +1132% | −68% | −84% | −89% | −85% |
| 12 | Δ% | +1567% | −87% | −98% | −98% | −100% |

Table 7f: Mean individual consumption (IC mg) and percent change (Δ%) in mean population number over time (weeks) in colonies of German cockroaches of the Las Palms resistant strain, offered food without (RC) or with (w/w) 1% xanthine and various concentrations of oxypurinol (OXY). The ratio of treated and untreated food consumed is given as a percent of the total amount eaten. (% TOTAL). (n = 3; 100% = 42)

Additional experiments were conducted to assess food choice. The diets offered were untreated rat chow alone (RC) for the control and a choice of untreated rat chow (RC) and rat chow treated (w/w) with 1% xanthine and various concentrations of oxypurinol.

The results, in Tables 7g and 7h, below, show a similar level of control of these populations compared to that exhibited in populations where no choice of diet was available (see Tables 7e and 7f). Mean individual consumption (ICmg) over the first three weeks showed little difference between the percentage of untreated and treated food consumed.

The amount of oxypurinol ingested in the choice tests was the least (450 μg) at the highest concentration (5%) for the Hawthorne strain, with 600 μg ingested at the 2% concentration, and 840 μg ingested at the 4% level. The amount ingested by the Las Palms strain was 660 μg at the 3% level and 900 μg at the 4% level. Population decline, however, was slower in the Las Palms colonies than in the Hawthorne colonies.

TABLE 7g

| TIME (wks) | TEST | CONTROL RC | RCX 2% RC | OXY | RCX 4% RC | OXY | RCX 5% RC | OXY |
|------|------|------|------|------|------|------|------|------|
| 3 | IC mg | 64 | 30 | 30 | 31 | 28 | 33 | 29 |
|   | ±SEM | ±1.4 | ±3.0 | ±5.0 | ±6.5 | ±4.2 | ±2.7 | ±5.6 |
| 3 | % TOTAL | 100% | 51% | 49% | 52% | 48% | 54% | 46% |
| 6 | Δ% | +871% | −50% | | −75% | | −77% | |
| 9 | Δ% | +1486% | −94% | | −96% | | −97% | |

Table 7g: Mean individual consumption (IC mg) and percent change (Δ%) in mean population number over time (weeks) in colonies of German cockroaches of the Hawthorne resistant strain offered untreated rat chow alone (RC), or untreated rat chow offered together as a choice of diet with rat chow treated (w/w) with 1% xanthine (X), and various concentrations of oxypurinol (OXY). The ratio of treated and untreated food consumed is given as a percent of the total amount eaten (% TOTAL). (n = 3; 100% = 42)

TABLE 7h

| TIME (wks) | TEST | CONTROL RC | RCX 3% OXY RC | | RCX 4% OXY RC | |
|------|------|------|------|------|------|------|
| 3 | IC mg | 60 | 25 | 22 | 29 | 23 |
|   | ±SEM | (±3.4) | (±3.7) | (±2.3) | (±2.1) | (±3.7) |
| 3 | % TOTAL | 100% | 53% | 47% | 56% | 44% |
| 6 | Δ% | +490% | −52% | | −43% | |
| 9 | Δ% | +1741% | −87% | | −83% | |
| 12 | Δ% | +1819% | −95% | | −97% | |

Table 7h: Mean individual consumption (IC mg) and percent change (Δ%) in mean population number over time (weeks) in colonies of German cockroaches of the Las Palms resistant strain offered untreated rat chow alone (RC), or untreated rat chow offered together as a choice of diet with rat chow treated (w/w) with 1% xanthine (X), and various concentrations of oxypurinol (OXY). The ratio of treated and untreated food consumed is given as a percent of the total amount eaten (% TOTAL). (n =3; 100% = 42)

Additional experiments were conducted to assess the effects of different xanthine-oxypurinol compositions. Colonies of Hawthorne and Las Palms strains were prepared as described. The diets administered consisted of rat chow (RC) or rat chow+bait base (50/50) (RCBB), or bait base alone (BB); each of which had been treated with 1% xanthine and either 1% or 2% oxypurinol. A control diet, consisting of untreated rat chow, also was administered.

Results are given in Tables 7i and 7j below, and show a faster rate of decline to extinction at seven or eight weeks in both strains, at concentrations of oxypurinol that compare with those used to control populations of the susceptible VPI strain.

TABLE 7i

| TIME | | CONTROL | 1% OXY | | 2% OXY | |
|---|---|---|---|---|---|---|
| (WKS) | TEST | RC | RCBBX | BBX | RCBBX | BBX |
| 3 | IC mg | 60 | 57 | 47 | 55 | 43 |
| | (±SEM) | (±1.1) | (±2.2) | (±1.4) | (±1.3) | (±0.6) |
| 3 | Δ% | −2% | −17% | −58% | −10% | −48% |
| 6 | Δ% | +684% | −94% | −100% | −87% | −99% |
| 8 | Δ% | >+684% | — | — | −97% | −100% |

Table 7i: Mean individual consumption (IC mg) and percent change (Δ%) in mean population number over time (weeks), in colonies of German cockroaches of the Hawthorne resistant strain offered untreated rat chow (RC) or food treated with 1% xanthine and various concentrations of oxypurinol (OXY). The food was either rat chow mixed 50% (w/w) with bait base (RCBB) or bait base alone (BB). (n = 3; 100% = 42)

TABLE 7j

| TIME | | RC | 1% OXY | | 2% OXY | |
|---|---|---|---|---|---|---|
| (WKS) | TEST | CONTROL | RCBBX | BBX | RCBBX | BBX |
| 3 | IC mg | 50 | 42 | 36 | 41 | 35 |
| | (±SEM) | (±1.1) | (±1.7) | (±0.9) | (±1.2) | (±2.3) |
| 3 | Δ% | −4% | −16% | −39% | −7% | −37% |
| 6 | Δ% | +491% | −56% | −97% | −47% | −82% |
| 7 | Δ% | >491% | −97% | −100% | −96% | −100% |

Table 7j: Mean individual consumption (IC mg) and percent change (Δ%) in mean population number over time (weeks), in colonies of German cockroaches of the Las Palms resistant strain offered untreated rat chow (RC) or food treated with 1% xanthine and various concentrations of oxypurinol (OXY). The food was either rat chow mixed 50% (w/w) with bait base (RCCB) or bait base alone (BB). (n = 3; 100% = 42)

Assessment of food choice was conducted as previously described. Choices were untreated bait base (BB), and bait base treated (w/w) with 1% xanthine and either 1% or 2% oxypurinol. Calculations were made as previously described, and the results are shown in Tables 7k and 7l.

There was little distinction made between untreated and treated food in both strains, with population growth being controlled to near extinction at six weeks, regardless of the slight reduction in consumption of food containing the higher oxypurinol concentration. The range of oxypurinol ingested over the first three weeks was 210–230 μg in the Hawthorne strain, and 150–180 μg for the Las Palms strain. The rate of population decline was comparable to that achieved when no choice of diet was offered. (See Tables 7i and 7j).

TABLE 7k

| TIME | | BB CONTROL | | BBX 1% OXY | | BBX 2% OXY |
|---|---|---|---|---|---|---|
| (wks) | TEST | | BB | | BB | |
| 3 | IC mg | 60 | 22 | 23 | 19 | 21 |
| | (SEM) | n = 1 | (±0.9) | (±1.3) | (±0.3) | (±1.5) |
| 3 | % TOTAL | 100% | 49% | 51% | 48% | 52% |
| 3 | Δ% | 0% | −62% | | −52% | |
| 4 | Δ% | −2% | −94% | | −92% | |
| 6 | Δ% | +328% | −98% | | −99% | |

Table 7k: Mean individual consumption (IC mg), consumption ratio (% TOTAL), and percent change (Δ%) in mean population numbers over time (weeks), in colonies of German cockroaches of the Hawthorne resistant strain, where untreated bait base (BB), and bait base treated (w/w) with 1% xanthine (X), and either 1% or 2% (w/w) oxypurinol (OXY), were offered as a choice of fool. (n = 3, 100% = 42)

TABLE 7l

| TIME | | BB CONTROL | | BBX 1% OXY | | BBX 2% OXY |
|---|---|---|---|---|---|---|
| (wks) | TEST | | BB | | BB | |
| 3 | IC mg | 47 | 17 | 18 | 16 | 15 |
| | (SEM) | n = 1 | (±0.6) | (±0.6) | (±0.9) | (±0.3) |
| 3 | % TOTAL | 100% | 49% | 51% | 51% | 49% |
| 3 | Δ% | 0% | −48% | | −43% | |
| 4 | Δ% | 0% | −84% | | −86% | |
| 6 | Δ% | +424% | −98% | | −99% | |

Table 7l: Mean individual consumption (IC mg), consumption ratio (% TOTAL), and percent change (Δ%) in mean population numbers over time (weeks), in colonies of German cockroaches of the Las Palms resistant strain, where untreated bait base (BB), and bait base treated (w/w) with 1% xanthine (X), and either 1% or 2% (w/w) oxypurinol (OXY), were offered as a choice of food. (n = 3, 100% = 42)

EXAMPLE 10

Treatment of Resistant Cockroaches with Xanthine-Trimethoprim Compositions

Colonies of cockroaches were prepared as described, using the Hawthorne and Las Palms resistant strains.

As shown in Table 8a below, for the Hawthorne strain, feeding was inhibited in relation to the control, in direct ratio to the concentration of trimethoprim in the diet. The maximum decrease of 62% occurred at a concentration of 4% trimethoprim, which represents a dose of 639 μg per individual over the first three weeks. Population growth of the Hawthorne strain was controlled at the higher concentrations.

TABLE 8a

| TIME | | | RCX + T % | | | | |
|---|---|---|---|---|---|---|---|
| (wks) | TEST | RC | 0.5 | 1.0 | 2.0 | 3.0 | 4.0 |
| 3 | IC mg | 42.5 | 37.6 | 37.1 | 30.4 | 17.2 | 15.9 |
| | (±SEM) | (±0.7) | (±2.1) | (±1.7) | (±2.0) | (±1.2) | (±1.4) |
| | | n = 7 | n = 3 | n = 3 | n = 6 | n = 6 | n = 3 |
| 3 | Δ% | −7% | −2% | −6% | −27% | −75% | −79% |
| | | n = 7 | n = 3 | n = 3 | n = 6 | n = 4 | n = 3 |
| 6 | Δ% | +368% | | | −70% | −79% | −89% |
| | | n = 4 | | | n = 3 | n = 4 | n = 3 |
| 9 | Δ% | +606% | +369% | +298% | −17% | −95% | −94% |
| | | n = 7 | n = 3 | n = 3 | n = 6 | n = 4 | n = 3 |

TABLE 8a-continued

| TIME | | | RCX + T % | | | | |
|---|---|---|---|---|---|---|---|
| (wks) | TEST | RC | 0.5 | 1.0 | 2.0 | 3.0 | 4.0 |
| 12 | Δ% | +913%<br>n = 3 | | | −51%<br>n = 3 | −93%<br>n = 3 | −97%<br>n = 3 |

Table 8a: Mean individual consumption (IC mg), and percent change (Δ%) in mean population numbers, in colonies of German cockroaches of the Hawthorne resistant strain offered food without (RC), or with 1% xanthine (RCX), and various concentrations (w/w) of trimethoprim (T %) over time (weeks).

For the Las Palms strain, as shown in Table 8b below, an even decline in ICmg of treated food occurred in direct relation to the increase in concentration of trimethoprim. The maximum inhibition, compared with the control, was 38% at a concentration of 6% trimethoprim, which constitutes an ingested dose of 1,758 μg per individual over three weeks. Population numbers were reduced by two-thirds at six weeks of treatment.

TABLE 8b

| TIME | | | RCX + T % | | | |
|---|---|---|---|---|---|---|
| (wks) | TEST | RC | 3.0 | 4.0 | 5.0 | 6.0 |
| 3 | IC mg<br>(±SEM) | 45.0<br>(±3.8) | 43.0<br>(±3.5) | 41.3<br>(±2.2) | 37.0<br>(±2.3) | 29.3<br>(±1.8) |
| 3 | Δ% | −12% | −24% | −26% | −43% | −57% |
| 6 | Δ% | +336% | +100% | −37% | −37% | −67% |

Table 8b: Mean individual consumption (IC mg) and percent change (Δ%) in mean population number, in colonies of German cockroaches of the Las Palms resistant strain offered food without (RC), or without 1% xanthine (RCX), and with various concentrations (w/w) of trimethoprim (T %) over time (weeks). n = 3

EXAMPLE 11

Treatment of Cockroaches with Xanthine-Oxypurinol-Trimethoprim Compositions

Colonies of German cockroaches of the VPI susceptible strain and colonies of the Hawthorne resistant strain were offered either untreated rat chow (RC), or rat chow treated (w/w) with 1% xanthine (RCX), combined with 2% oxypurinol (OXY) and either 2% or 4% trimethoprim (T). Results are shown in Tables 9a (VPI strain) and 9b (Hawthorne strain). In both, colonies were virtually extinct by six weeks of treatment, in spite of declines in mean individual consumption (ICmg) of greater than 50%.

TABLE 9a

| TIME<br>(wks) | TEST | RC | RCX + 2% OXY + 2% T |
|---|---|---|---|
| 3 | IC mg<br>(±SEM) | 71.3<br>n = 1 | 34.9<br>(±1.6) |
| 3 | Δ% | −5% | −68% |
| 6 | Δ% | +955% | −99% |

Table 9a: Mean individual consumption (IC mg) and percent change (Δ%) in mean population number over time (weeks), in colonies of German cockroaches of the VPI susceptible strain offered food without (RC), or with (w/w) 1% xanthine (RCX) and 2% oxypurinol (OXY) and 2% trimethoprim (T). (n = 3, 100% = 42)

TABLE 9b

| TIME<br>(wks) | TEST | RC | RCX + 2% OXY + 4% T |
|---|---|---|---|
| 3 | IC mg<br>(±SEM) | 72<br>n = 1 | 34.1<br>(±0.6) |
| 3 | Δ% | −2.4% | −76% |
| 6 | Δ% | +1416% | −98% |

Table 9b: Mean individual consumption (IC mg), and percent change (Δ%) in mean population number over time (weeks), in colonies of German cockroaches of the Hawthorne resistant strain offered food without (RC), or with (w/w) 1% xanthine (RCX), 2% oxypurinol (OXY), and 4% trimethoprim (T). (n = 3, 100% = 42)

In additional experiments, colonies of the VPI susceptible strain and colonies of the Las Palms resistant strain were prepared as already described. The VPI strain was offered food composed of rat chow alone (RC) or rat chow treated (w/w) with 1% xanthine (X), 2% oxypurinol (OXY), and 1% trimethoprim (T). The Las Palms strain was offered either rat chow alone (RC), or rat chow treated (w/w) with 1% xanthine (X), 3% oxypurinol (OXY), and 4% trimethoprim (T).

Mean individual consumption (ICmg), and percent change (Δ%) in mean population number were calculated as described previously.

The results are given in Table 9c, below, and show that, while there was a reduction in the rate of feeding, there was a considerable decline in the treated populations, leading to extinction by the sixth week. The disparate concentrations in the compositions resulted in the same rate of decline in the susceptible and resistant insects, indicating that manipulation of the components can result in parity of population control, even where there are major differences in the insect strains.

TABLE 9c

| | | VPI | | LAS PALMS | |
|---|---|---|---|---|---|
| TIME<br>(wks) | TEST | RC | RCX<br>2% OXY +<br>1% T | RC | RCX<br>3% OXY +<br>4% T |
| 3 | IC mg<br>(±SEM) | 76<br>n = 1 | 50<br>(±2.0) | 60<br>n = 1 | 35<br>(±1.5) |
| 3 | Δ% | −2% | −48% | −10% | −34% |
| 6 | Δ% | +1562% | −77% | +679% | −79% |
| 9–10 | Δ% | >+1562% | −98% | +1819% | −99% |

Table 9c: Mean individual consumption (IC mg) and percent change (Δ%) in mean population number over time (weeks) in colonies of German Cockroaches of the VPI susceptible strain and the Las Palms resistant strain, each offered untreated food (RC) or food treated (w/w) with 1% xanthine and various concentrations of oxypurinol and trimethoprim. (n = 3, 100% = 42)

The ratios used in the trials summarized in Table 9c were X:OXY:T of 1:2:1 and 1:3:4. Additional concentration ratios were assessed, as summarized in Tables 9d and 9e, below, by administering the following diets to colonies of the susceptible VPI strain: rat chow+bait base; bait base; rat chow+bait base treated (w/w) with 1% xanthine and 1% oxypurinol (OXY), plus either 0.1% or 0.5% trimethoprim (T).

Little difference in mean individual consumption was observed in insects fed the control diets and those fed compositions containing trimethoprim. However, although the inclusion of trimethoprim caused some feeding inhibition, the decline in populations was slightly faster with the higher trimethoprim concentration (0.5%) than with the lower concentration (0.1%).

The amount of trimethoprim ingested at these concentrations was 41 µg and 190 µg respectively in the first trial, while that of oxypurinol was 510 µg, 410 µg, and 380 µg (Table 9d). In the second trial, the rate for trimethoprim was 30 µg and 165 µg, while for oxypurinol it was 400 µg, 300 µg, and 330 µg, respectively.

TABLE 9d

|  |  |  | RCBBX | |
| --- | --- | --- | --- | --- |
| TIME (WKS) | TEST | RCBB CONTROL | 1% OXY | 1.0% OXY 0.1% T | 1% OXY 0.5% T |
| 3 | IC mg (±SEM) | 63 (±2.7) | 51 (±2.0) | 41 (±1.2) | 38 (±1.7) |
| 3 | Δ% | −6% | −35% | −45% | −56% |
| 6 | Δ% | +462% | −92% | −92% | −100% |

Table 9d: Mean individual consumption (IC mg) and percent change (Δ%) in mean population number over time (weeks) in colonies of German cockroaches of the VPI susceptible strain offered rat chow mixed 50% (w/w) with bait base either untreated (RCBB), or treated (w/w) with 1% xanthine (X), 1% oxypurinol (OXY), and either 0.1% or 0.5% trimethoprim (T). (n = 3; 100% = 42)

TABLE 9e

|  |  |  | BBX | |
| --- | --- | --- | --- | --- |
| TIME (wks) | TEST | BB CONTROL | 1% OXY | 1% OXY 0.1% T | 1% OXY 0.5% T |
| 3 | IC mg (±SEM) | 67 (±2.6) | 40 (±1.8) | 30 (±1.0) | 33 (±2.0) |
| 3 | Δ% | −6% | −59% | −55% | −79% |
| 6 | Δ% | +738% | −97% | −99% | −100% |

Table 9e: Mean individual consumption (IC mg) and percent change (Δ%) in mean population number over time (weeks), in colonies of German cockroaches of the VPI susceptible strain offered bait base either untreated (BB), or treated (w/w) with 1% xanthine (X), 1% oxypurinol (OXY), and either 0.1% or 0.5% trimethoprim (T). (n = 3; 100% = 42)

EXAMPLE 12

Assessment of Purines with Oxypurinol or Trimethoprim

Colonies of cockroaches of the VPI susceptible strain were prepared essentially as described in Example 1. The diets administered were rat chow alone (RC), or rat chow (w/w) with 3% trimethoprim and either 1% xanthine (X), 1% hypoxanthine (H), or 1% guanine (G). Mean individual consumption (ICmg) and percent change (Δ%) in mean population number were calculated as before, with the results shown in Table 10 below.

The results, with hypoxanthine and guanine replacing the xanthine component of the diet mixtures, compared closely with those obtained with xanthine. Population growth was controlled to extinction of the colonies, although some feeding inhibition occurred with all of the trimethoprim compositions.

TABLE 10

| TIME |  | RC | RC +3% T | | |
| --- | --- | --- | --- | --- | --- |
| (wks) | TEST | CONTROL | 1% X | 1% H | 1% G |
| 3 | IC mg (±SEM) | 54 (±0) | 26 (±8.0) | 25 (±7.0) | 29 (±8.0) |
| 3 | Δ% | −5.5% | −68 | −74 | −71 |
| 6 | Δ% | +152 | −99 | −91 | −83 |
| 9 | Δ% | +1426 | −100 | −100 | −100 |

Table 10: Mean individual consumption (IC mg), and percent change (Δ%) in mean population number over time (weeks), in colonies of German cockroaches of the VPI susceptible strain offered rat chow untreated (RC), or treated (w/w) with 3% trimethoprim (T), and 1% of a purine. Purines were xanthine (X), hypoxanthine (H), or guanine (G). (n = 2, 100% = 42)

Additional experiments were conducted to assess the effects of the same purines in combination with oxypurinol. Colonies of German cockroaches of the VPI susceptible strain were prepared as described. The diets administered were either rat chow alone (RC), rat chow treated (w/w) with 1% guanine (G), and either 1% or 2% oxypurinol (OXY), or rat chow treated with 2% guanine and either 1% or 2% oxypurinol. Calculations were made as before. As shown in Table 11 below, the results obtained with guanine were much the same as those obtained with xanthine.

TABLE 11

|  |  | RC | RC + 1% G | | RC + 2% G | |
| --- | --- | --- | --- | --- | --- | --- |
| TIME (WKS) | TEST | CON- TROL | 1% OXY | 2% OXY | 1% OXY | 2% OXY |
| 3 | IC mg (±SEM) | 66.5 (±0.5) | 64 (±1.5) | 64 (±2.4) | 64 (±1.0) | 64.0 (±2.0) |
| 3 | Δ% | −7% | −12% | −15% | −5% | −11% |
| 6 | Δ% | +1262% | −83% | −71% | −83% | −74% |
| 9 | Δ% | +1257% | −99.5% | −100% | −98% | −100% |

Table 11: Mean individual consumption (IC mg) and percent change (Δ%) in mean population numbers over time (weeks) in colonies of German cockroaches of the VPI susceptible strain offered food without (RC), or with (w/w) 1% or 2% guanine (G), and 1% or 2% oxypurinol (OXY). (n = 2; 100% = 42)

In Table 12, results are shown for a similar trial utilizing hypoxanthine (HX) and either 1% or 2% oxypurinol. Little difference in ICmg was observed across these two trials, and the activity of the oxypurinol was enhanced in the same manner as when it was administered with xanthine.

TABLE 12

| TIME |  | RC | RC + 1% H | |
| --- | --- | --- | --- | --- |
| (wks) | TEST | CONTROL | 1% OXY | 2% OXY |
| 3 | IC mg (±SEM) | 63 (±4.8) | 42 (n = 1) | 62 (±1.2) |
| 3 | Δ% | −5% | −17% | −24% |
| 6 | Δ% | +762% | −83% | −30% |
| 9 | Δ% | +1452% | −100% | −95% |

Table 12: Mean individual consumption (IC mg) and percent change (Δ%) in mean population number over time (weeks) in colonies of German cockroaches fed a diet of untreated rat chow (RC), or rat chow treated (w/w) with 1% hypoxanthine (HX), and either 1% or 2% oxypurinol (OXY). (n = 3; 100% = 42)

Additional studies were conducted to assess compositions containing 1% purine, which, in these trials, was either guanine (G), or hypoxanthine (H), with 2% oxypurinol and either 1% or 2% trimethoprim (T). Calculations were made as before, and the results shown in Table 13, below.

Both of the purines in this trial acted in the same manner as xanthine in boosting the activity of the other components in each composition, leading to extinction of the treated colonies by the sixth week. Decline was rapid in all cases, despite some feeding inhibition at the higher concentrations of trimethoprim.

TABLE 13

| TIME | RC | RC + 2% OXY | | | |
|---|---|---|---|---|---|
| | | 1% G | | 1% H | |
| (WKS) | TEST | CONTROL | 1% T | 2% T | 1% T | 2% T |
| 3 | IC mg | 68 | 46 | 26 | 41 | 34 |
| | (±SEM) | (±4.0) | (±1.5) | (±3.7) | (±2.2) | (±2.7) |
| 3 | Δ% | −1% | −59% | −78% | −58% | −76% |
| 6 | Δ% | +1423% | −100% | −98% | −100% | −100% |

Table 13: Mean individual consumption (IC mg) and percent change (Δ%) in population number over time (weeks), in colonies of German cockroaches of the VPI susceptible strain offered rat chow without (RC), or treated with 2% oxypurinol (OXY), 1% of either guanine (G) or hypoxanthine (HX), and 1% or 2% trimethoprim (T). (n = 3, 100% = 42)

To further determine the effects of compositions using other purines in place of the xanthine component, uric acid (UA), the "terminal" product of the purine metabolic pathway (see FIG. 1), was combined with allopurinol (ALL), a member of the class of metabolic-enzyme inhibitors which includes oxypurinol. Colonies of cockroaches were prepared essentially as described in Example 1. The diets administered were either rat chow alone (RC), or rat chow treated (w/w) with 1% UA, and 1% or 2% ALL.

Mean individual consumption (ICmg) and percent change (Δ%) in mean population number were calculated as before, and the results shown in Table 14, below. Steady declines of the treated populations were observed, despite some feeding inhibition compared with untreated controls.

TABLE 14a

| TIME | RC | 1% UA | |
|---|---|---|---|
| (wks) | TEST | CONTROL | 1% ALL | 2% ALL |
| 3 | IC mg | 58 | 49 | 46 |
| | (±SEM) | n = 1 | (±1.2) | (±4.5) |
| 3 | Δ% | −7% | −7% | −9% |
| 6 | Δ% | +379% | −33% | −27% |
| 9 | Δ% | +1098% | −57% | −54% |

Table 14: Mean individual consumption (IC mg) and percent change (Δ%) in mean population number over time (weeks), in colonies of German cockroaches of the VPI susceptible strain offered untreated rat chow (RC), or rat chow treated (w/w) with 1% uric acid (UA), and either 1% or 2% allopurinol (ALL). (n = 3, 100% = 42)

In a further experiment, a composition of uric acid and oxypurinol was administered to replicate colonies of cockroaches, prepared essentially as described in Example 1. The diets administered were either bait base alone (BB), or bait base treated (w/w) with 1% uric acid (UA) and 1.0% oxypurinol (OXY).

Mean individual consumption (ICmg) and percent change (Δ%) in mean population number were calculated as before, and the results are shown in Table 14b. The treated populations declined steadily, as predicted.

TABLE 14b

| TIME (wks) | TEST | BB CONTROL | BB + 1% UA 1% OXY |
|---|---|---|---|
| 3 | IC mg | 58 | 51 |
| | (±SEM) | (±3.8) | (±2.0) |
| 3 | Δ% | −6% | −40% |
| 6 | Δ% | >100% | −98% |

Table 14b: Mean individual consumption (IC mg), and percent change (Δ%) in mean population numbers over time (weeks), in colonies of German cockroaches of the AMCY susceptible strain offered untreated bait base (BB), or bait base treated (w/w) with 1% uric acid (UA), and 1% oxypurinol (OXY). (n = 3; 100% = 42)

EXAMPLE 13

Comparison of Trimethoprim Activity With Other Dihydrofolate Reductase Inhibitors Additional experiments were conducted to compare the activity of compositions with xanthine and either trimethoprim (T), or methotrexate (M), which is a dihydrofolate reductase inhibitor with activity similar to trimethoprim. Colonies of German cockroaches of the VPI susceptible strain were prepared essentially as described in Example 1. The diets administered were either untreated rat chow (RC), or rat chow treated (w/w) with 1% xanthine (X), and either 2% trimethoprim (T), or 2% methotrexate (M). Results were calculated as previously described, and are shown in Table 15, below.

The experiments were terminated after three weeks of treatment, but the results show that, although there was some feeding inhibition in the treated colonies, the populations were declining steadily. The effects with methotrexate were slower than with trimethoprim, but showed the same patterns of mortality among the age groups as described for trimethoprim, with the nymphs dying early.

TABLE 15

| TIME | RC | RC + 1% X | |
|---|---|---|---|
| (wks) | TEST | CONTROL | 2% T | 2% M |
| 3 | IC mg | 67 | 33 | 41 |
| | (±SEM) | (±4.8) | (±0.5) | (±2.0) |
| 3 | Δ% | −3% | −89% | −45% |

Table 15: Mean individual consumption (IC mg) and percent change (Δ%) in population number over time (weeks), in colonies of German cockroaches of the VPI susceptible stain offered untreated rat chow (RC), or rat chow treated with 1% xanthine (X) and either 2% trimethoprim (T), or 2% methotrexate (M). (n = 3, 100% = 42)

EXAMPLE 14

Comparison of Activity Levels of Oxypurinol with other Purine Metabolic Enzyme Inhibitors Additional experiments were conducted to assess the effects of compositions consisting of xanthine and purine metabolic-enzyme inhibitors included, with oxypurinol, in the group of pyrazolo[3,4-d]pyrimidine compounds described previously.

In the first of these comparisons, replicate colonies of German cockroaches were prepared essentially as described in Example 1. The diets administered were either untreated rat chow (RC), or rat chow treated (w/w) with 1% xanthine (X), and 1% or 2% of either oxypurinol (OXY), or allopurinol (ALL). Results were calculated as previously described, and are shown in Table 16, below.

TABLE 16

| TIME | TEST | RC CONTROL | RC + 1% X | | RC + 1% X | |
|---|---|---|---|---|---|---|
| | | | 1% OXY | 2% OXY | 1% ALL | 2% ALL |
| 3 | IC mg | 63 | 68 | 68 | 66 | 63.3 |
|   | (±SEM) | (±1.5) | (±1.8) | (±2.1) | (±2.1) | (±2.7) |
| 3 | Δ% | −4% | −10% | −14% | −9% | −16% |
| 6 | Δ% | +1390% | −60% | −56% | −39% | −51% |
| 9 | Δ% | +1464% | −99% | −98% | −71% | −73% |
| 12 | Δ% | +1859% | −100% | −100% | −92% | −94% |

Table 16: Mean individual consumption (IC mg) and percent change (Δ%) in mean population number over time (weeks), in colonies of German cockroaches of the VPI susceptible strain offered untreated rat chow (RC), or rat chow treated (w/w) with 1% xanthine (X), and either 1% or 2% oxypurinol (OXY), or 1% or 2% allopurinol (ALL). (n = 3; 100% = 42)

Not much difference in mean individual consumption of food was observed among the groups, with the biggest difference noted with colonies fed compositions containing 2% allopurinol. However, the rate of decline in population was much faster with oxypurinol, which showed marked effects three weeks in advance of the compositions with allopurinol.

In the second comparison, replicate colonies of cockroaches of the American Cyanamid (AMCY) susceptible strain were prepared essentially as described in previous examples. The diets administered were untreated bait base (BB), or bait base treated (w/w) with 1% xanthine (X), and with either 1% oxypurinol (OXY), or 0.5% mercapto-allopurinol (MAL) (Synthons, Inc., Blacksburg, Va.). Mean individual consumption (ICmg) and percent change (Δ%) in mean population numbers were calculated as before, with the results shown in Table 17, below.

TABLE 17

| TIME | | BB | BB + 1% X | |
|---|---|---|---|---|
| (wks) | TEST | CONTROL | 1% OXY | 0.5% MAL |
| 2 | IC mg | 37 | 37 | 18 |
|   | (±SEM) | (±2.5) | (±0.6) | (±1.0) |
| 1 | Δ% | −0% | −4% | −15% |
| 2 | Δ% | −2% | −44% | −70% |
| 3 | Δ% | −2% | −79% | −93% |

Table 17: Mean individual consumption (IC mg), and percent change (Δ%) in mean population numbers over time (weeks), in colonies of German cockroaches of the AMCY susceptible strain offered untreated bait base (BB), or bait base treated with 1% xanthine, and either 1% oxypurinol (OXY), or 0.5% mercapto-allopurinol (MAL). (n = 3; 100% = 42)

Over the first two weeks, the amount of mercapto-allopurinol allopurinol ingested was 90 μg per insect, but even with this comparatively low consumption rate, the populations declined rapidly. For oxypurinol, the amount ingested was 370 μg per insect over the first two weeks, with the activity of the oxypurinol composition lagging behind that of mercapto-allopurinol.

In examining their in vitro properties in light of the results obtained here, it has become evident that the half-reaction times of the pyrazolo[3,4-d]pyrimidines can be used to roughly predict their activity in vivo when combined with xanthine, or perhaps with other of the purines. For example, of the three examined here, mercapto-allopurinol has an in vitro half-reaction time that is about four times longer than that of oxypurinol. As can be seen in Table 17, that fact is reflected in the accelerated mortality rate this compound achieved when combined with xanthine.

These results suggest that others in this group of related compounds could be used in compositions with xanthine, or with other of the purines described, to effect population control in cockroaches and other insects.

EXAMPLE 15

Treatment of Insects Other Than Cockroaches with Xanthine-Oxypurinol Compositions Additional experiments were conducted to assess the effects of the compositions on pest insects other than cockroaches. The results of these experiments support the claim that treatment with xanthine-oxypurinol compositions inhibits the mobilization of vital nutritional resources in insects which salvage, store, or excrete their nitrogenous wastes via the purine metabolic pathway.

1). House Flies

To determine the effects of the compositions on the house fly *Musca domestica*, two methods were employed. In the first, fifteen replicate groups of five each of four-day-old male and female adult flies from the same cohort were placed in mesh-screened cages. They were supplied with food and water, and allowed to mate and to lay eggs.

For oviposition, each cage was supplied with a plastic cup containing 340 g of wetted Chemical Specialties Manufacturer's Association larval growth medium (CSMA) (Purina Mills, Inc.). The medium was either untreated, or treated (w/w) with either 0.25% xanthine (X) and 0.25% oxypurinol (OXY), or 0.5% xanthine and 0.5% oxypurinol.

The cups of CSMA were removed after 48 hours, tightly covered with muslin to prevent the larvae escaping, and each cup was shelved adjacent to its parent cage. A container of fresh CSMA medium was offered for oviposition, as before, for a further 48 hours, after which the adult flies were discarded.

Both CSMA cups were returned to their parent cage, where the larvae were allowed to develop, pupate, emerge as adults, and die. The number of dead adults in each cage was counted and recorded. The mean number of adult flies that emerged from each treatment group, and the percent change (Δ%) in the number of emerged adults in the treated groups in relation to the untreated (control) groups were calculated, and the results are shown in Table 18a.

Statistical analysis showed that the mean number of adult flies that emerged from the treated CSMA medium was significantly lower than that from the untreated CSMA, regardless of treatment concentration. This was shown using paired T-tests (df=7; P-<0.01, for both treatments) (Microsoft Excel Ver. 5.0).

TABLE 18a

| TEST | CONTROL | 0.25% X 0.25% OXY | 0.5% X 0.5% OXY |
|---|---|---|---|
| TOTAL # | 4,374 | 1,170 | 858 |
| MEAN # | 875 | 234 | 172 |
| (±SEM) | (±74) | (±32) | (±49) |
| Δ% | 100% | −73% | −80% |

Table 18a: Total number and mean number of emerged adult house flies, and percent difference in mean emergence between treated and untreated larvae (Δ%) reared either in CSMA medium untreated (CONTROL), or treated (w/w) with either 0.25% xanthine (X) and 0.25% oxypurinol (OXY), or 0.5% xanthine and 0.5% oxypurinol. (n = 5)

In the second method, groups of 100 house fly eggs that were less than 12 hours old were placed into cups of 340 grams of wetted CSMA medium which was either untreated, or treated as described for the first method. There were five replicates for each treatment. The cups were covered with muslin cloth, and were incubated at 30° C. with 80% relative humidity until the eggs had hatched and the fly larvae had developed, pupated, emerged as adult flies, and died.

The number of pupal cases and dead adults in each container were counted, and the mean number of pupae and adults for each treatment, and the percent loss in adult population number ($\Delta\%$) for each treatment were calculated. These results are shown in Table 18b.

Statistical analysis showed that there was no significant difference in the mean number of pupae in each treatment shown by analysis of variance ($\alpha=0.05$, P=0.305, df-2; F=1.311) (Microsoft Excel Ver. 5.0). There was, however, an obvious difference in the mean number of adults that emerged successfully.

TABLE 18b

| TEST | CONTROL | | 0.25% X 0.25% OXY | | 0.5% X 0.5% OXY | |
|---|---|---|---|---|---|---|
| STAGE | PUPAE | ADULTS | PUPAE | ADULTS | PUPAE | ADULTS |
| TOTAL # | 375 | 363 | 333 | 37 | 324 | 29 |
| MEAN # | 75 (±2.4) | 73 (±3.6) | 67 (±3.2) | 7 (±1.7) | 65 (±7.2) | 6 (±2.0) |
| $\Delta\%$ | | | | −3% | | −89% | | −91% |

Table 18b: Total number and mean number of pupae and emerged adult house flies, and percent difference in mean emergence between treated and untreated larvae ($\Delta\%$) reared either in CSMA medium untreated (CONTROL)1 or treated (w/w) with either 0.25% xanthine (X) and 0.25% oxypurinol (OXY), or 0.5% xanthine and 0.5% oxypurinol. (n = 5)

The data from both experimental methods confirm that adult house fly population numbers are greatly reduced when the larvae are treated with xanthine-oxypurinol compositions, although the pupation rate is similar whether the composition is present in the larval growth-medium or not. This confirms that the impact of treatment with the compositions is due to lack of the nutritional reserves which, in the normal course, enable the larvae to transform to adult flies.

2). Carpenter Ants

To determine the effects of xanthine-oxypurinol compositions on carpenter ants (*Camponotus pennsylvanicus*), replicate colonies were prepared in four small glass dishes (125 mm×65 mm), having a 15 mm diameter side-arm to allow the introduction of food containers. Each colony consisted of at least 100 ant larvae and 10 attendant adult ants, taken from field-collected colonies.

The colonies were offered a standard gel bait base either untreated (two colonies), or treated with 0.5% xanthine and 0.5% oxypurinol (two colonies). The food was offered in 1.5 ml microcentrifuge tubes which were weighed daily to determine consumption.

The ant larvae were allowed to develop and pupate. When more than half of the larvae had pupated, 50 pupae from each colony were removed to separate dishes where the adults were allowed to emerge. Ten attendant ants were included with these pupae.

Regular inspections of both treated and control colonies showed no difference in larval mortality or pupation. Mean daily consumption of bait was also similar, with 0.49 g (±0.20 g) consumed in the untreated control colonies, and 0.44 g (±0.18 gm) consumed in the treated colonies. However, the mean number of adults that emerged was 45% lower in the treated colonies than in the untreated colonies.

3) Termites

Colonies of approximately 1000 one-week-old Formosan termites (*Coptolermes formosanus*) were established in one-quart glass Mason jars half filled with blasting sand dampened with distilled water. These colonies were kept at room temperature and ambient humidity, and food consumption, and termite mortality were monitored regularly for 25 days.

The diets administered were either untreated powdered cellulose (Sigma), or cellulose treated with 1% xanthine, or cellulose treated with 1% xanthine and either 0.1%, 0.5% or 1.0% oxypurinol. The diets were slightly dampened with distilled water and packed into 1.5 ml microcentrifuge tubes which were placed on the surface of the sand in each jar.

There was little difference noted in food consumption between the untreated and treated baits, regardless of composition concentrations. Observations of relative mortality at 15, 20, and 25 days are shown in Table 18c.

TABLE 18c

| TIME (days) | CONTROL | 1% X | 1% X | | |
|---|---|---|---|---|---|
| | | | 0.1% OXY | 0.5% OXY | 1.0 OXY |
| 15 | + | + | ++ | ++ | ++ |
| 20 | + | ± | +++ | +++ | +++ |
| 25 | + | ± | +++ | +++ | +++ |

Table 18c: Relative mortality over time (days) in colonies of Formosan termites administered diets of cellulose either untreated, or treated with 1% xanthine alone (X), or 1% xanthine with either 0.1%, 0.5%, or 1.0% oxypurinol (OXY).
(+ = few dead, ± = half dead, ++ = many dead, +++ = most dead)

These results indicate that there is an effect on termite health when they are treated with xanthine alone, and that treatment with low concentrations of xanthine-oxypurinol compositions causes a decline in population.

4) Mole Crickets

To study the effects of the composition on the Southern mole cricket *Scapteriscus borellii*, adult crickets were obtained from sound-baited calling traps located on a golf course in Brunswick Co., NC. Male and female crickets were confined together to ensure that mating occurred.

Forty PVC tubes 15 cm long×7.5 cm diameter were filled with a uniform mixture of moist sandy soil, and closed at each end with clear plastic petri dish lids. The tubes were placed upright on trays in a greenhouse under normal day-length regime, and single female crickets were introduced into each of the tubes.

Twenty of the crickets were administered untreated, finely-ground cricket chow (Purina Mills, Inc.), and the remaining twenty were administered cricket chow treated with 2% xanthine and 2% oxypurinol. The food was protected from fungal contamination by the addition of 0.3% potassium sorbate (Sigma), and was placed directly onto the surface of the soil in the tube.

Each tube was examined daily for egg masses which the female laid in the petri dish on the bottom of the tube. The date of oviposition, and the number and weight of eggs in each egg-mass were recorded.

There was no apparent difference in food consumption between the two treatments, no mortality was noted that could be attributed to the effects of the diet, and only half of the females laid eggs in each group. However, there was a distinct shift in oviposition time in the treated group, where 80% of treated females that laid eggs did so after the 16th day, whereas 70% of the untreated females that laid eggs did so before the 16th day.

These experiments on different species of insects showed that when the nutritional resources of the insects were mobilized suddenly, as in pupation and adult emergence of house flies and carpenter ants, the result was a dramatic decline in the adult population. When the treated insects used their stored nutrients more gradually, the effects were less precipitous, as was the case with the termites.

The response in the treated mole crickets aligned with that of older adult cockroaches, and supports the contention that nutritional storage needs to be prevented by treatment with the composition in order to effect population control in any given species.

It is expected that compositions with the same component ratios described in the Examples, albeit with the concentrations of the individual components in proportion to body size, could be used to effect population control in insects of varying sizes.

All references cited herein are hereby incorporated by reference in their entireties.

What is claimed is:

1. A composition for controlling an insect pest which salvages, stores, or excretes its nitrogenous wastes via the purine metabolic pathway, comprising a purine selected from the group consisting of xanthine, hypoxanthine, guanine and mixtures thereof, in an amount of about 0.25% to about 2.0%, by weight; and a xanthine oxidase inhibitor selected from the group consisting of allopurinol, oxypurinol, mercapto-allopurinol, 4-mercapto,6-hydroxypyrazolo[3,4-d]pyrimidine, 4,6-dimercaptopyrazolo[3,4-d]pyrimidine, 4-amino,6-hydroxypyrazolo[3,4-d]pyrimidine, and mixtures thereof, in an amount of about 0.25% to about 2.0%, by weight.

2. A composition according to claim 1, wherein the insect pest is selected from the group consisting of house flies, termites, carpenter ants, and mole crickets.

3. A composition according to claim 2, wherein the insect pest is a housefly, the purine is xanthine, in an amount from about 0.25% to about 0.50%, by weight, and the xanthine oxidase inhibitor is oxypurinol, in an amount of about 0.25% to about 0.50%, by weight.

4. A composition according to claim 3, wherein the amount of xanthine is about 0.25%, by weight, and the amount of oxypurinol is about 0.25%, by weight.

5. A composition according to claim 3, wherein the amount of xanthine is about 0.50%, by weight, and the amount of oxypurinol is about 0.50%, by weight.

6. A composition according to claim 2, wherein the insect pest is a termite, the purine is xanthine, in an amount of about 1.0%, by weight, and the xanthine oxidase inhibitor is oxypurinol, in an amount of about 0.1% to about 1.0%, by weight.

7. A composition according to claim 6, wherein the amount of oxypurinol is about 0.1%, by weight.

8. A composition according to claim 6, wherein the amount of oxypurinol is about 0.5%, by weight.

9. A composition according to claim 6, wherein the amount of oxypurinol is about 1.0%, by weight.

10. A composition according to claim 2, wherein the insect is a carpenter ant, the purine is xanthine, in an amount of about 0.5%, by weight, and the xanthine oxidase inhibitor is oxypurinol, in an amount of about 0.5%, by weight.

11. A composition according to claim 2, wherein the insect is a mole cricket, the purine is xanthine, in an amount of about 2.0%, by weight, and the xanthine oxidase inhibitor is oxypurinol, in an amount of about 2.0%, by weight.

12. A method for controlling an insect pest which salvages, stores, or excretes its nitrogenous wastes via the purine metabolic pathway, which comprises bringing into contact with said insect pest, a growth-controlling amount of a composition comprising a purine selected from the group consisting of xanthine, hypoxanthine, guanine, and mixtures thereof, in an amount of about 0.25% to about 2.0%, by weight; and a xanthine oxidase inhibitor selected from the group consisting of allopurinol, oxypurinol, mercapto-allopurinol, 4-mercapto,6-hydroxypyrazolo[3,4-d]pyrimidine, 4,6-dimercaptopyrazolo[3,4-d]pyrimidine, 4-amino, 6-hydroxypyrazolo[3,4-d]pyrimidine, and mixtures thereof, in an amount of about 0.25% to about 2.0%, by weight.

13. A method according to claim 12, wherein the insect pest is a housefly, the purine is xanthine, in an amount from about 0.25% to about 0.50%, by weight, and the xanthine oxidase inhibitor is oxypurinol, in an amount of about 0.25% to about 0.50%, by weight.

14. A method according to claim 13, wherein the amount of xanthine is about 0.25%, by weight, and the amount of oxypurinol is about 0.25%, by weight.

15. A method according to claim 13, wherein the amount of xanthine is about 0.50%, by weight, and the amount of oxypurinol is about 0.50%, by weight.

16. A method according to claim 12, wherein the insect pest is a termite, the purine is xanthine, in an amount of about 1.0%, by weight, and the xanthine oxidase inhibitor is oxypurinol, in an amount of about 0.1% to about 1.0%, by weight.

17. A method according to claim 16, wherein the amount of oxypurinol is about 0.1%, by weight.

18. A method according to claim 16, wherein the amount of oxypurinol is about 0.5%, by weight.

19. A method according to claim 16, wherein the amount of oxypurinol is about 1.0%, by weight.

20. A method according to claim 12, wherein the insect is a carpenter ant, the purine is xanthine, in an amount of about 0.5%, by weight, and the xanthine oxidase inhibitor is oxypurinol, in an amount of about 0.5%, by weight.

21. A method according to claim 12, wherein the insect is a mole cricket, the purine is xanthine, in an amount of about 2.0%, by weight, and the xanthine oxidase inhibitor is oxypurinol, in an amount of about 2.0%, by weight.

* * * * *